United States Patent
Elworthy et al.

(10) Patent No.: US 6,900,336 B2
(45) Date of Patent: May 31, 2005

(54) 8-AZA-11-DEOXY PROSTAGLANDIN ANALOGUES

(75) Inventors: Todd Richard Elworthy, Los Gatos, CA (US); Tara Mirzadegan, Los Altos, CA (US); Michael Garret Roepel, San Francisco, CA (US); David Bernard Smith, San Mateo, CA (US); Keith Adrian Walker, Los Altos Hills, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 336 days.

(21) Appl. No.: 10/197,353

(22) Filed: Jul. 16, 2002

(65) Prior Publication Data

US 2003/0120079 A1 Jun. 26, 2003

Related U.S. Application Data

(60) Provisional application No. 60/371,348, filed on Apr. 10, 2002, and provisional application No. 60/305,727, filed on Jul. 16, 2001.

(51) Int. Cl.[7] ............................................. C07D 207/12
(52) U.S. Cl. ...................................... 548/551; 548/543
(58) Field of Search ................................. 548/551, 543

(56) References Cited

U.S. PATENT DOCUMENTS

| | | | |
|---|---|---|---|
| 3,975,399 A | 8/1976 | DeFranco et al. | |
| 4,113,873 A | 9/1978 | Himizu et al. | |
| 4,115,401 A | 9/1978 | Nanthavong et al. | |
| 4,177,346 A | 12/1979 | Nelson | |
| 4,320,136 A | 3/1982 | Scribner | |

FOREIGN PATENT DOCUMENTS

| | | |
|---|---|---|
| BE | 841165 | 10/1976 |
| EP | 1 110 949 A1 | 6/2001 |
| GB | 1553595 | 10/1979 |
| GB | 1569982 | 6/1980 |
| GB | 1583163 | 1/1981 |
| WO | WO 00/21532 A1 | 4/2000 |
| WO | WO 00/21542 A1 | 4/2000 |
| WO | WO 01/46140 A1 | 6/2001 |
| WO | WO 02/24647 A1 | 3/2002 |
| WO | WO 02/42268 A2 | 5/2002 |

OTHER PUBLICATIONS

Zoretic et al., "Synthesis of (E)–7–[[2–[4(m–Trifluoromethylphenoxy)–3α and 3β—Hydroxy–1–butenyl]–5–oxo–1–pyrrolidinyl]]heptanoic Acids", *J. Heterocyclic Chem.*, Mar.–Apr. 1983, pp. 465–466, 20.

Saijo, et al., "Heterocyclic prostaglandins. IV. Synthesis of 8–aza–11–deoxyprostaglandin E, and its related compounds," *Yakugaku Zashi*, 1980, pp. 3890–3895, 100(4), ABSTRACT.

Suda, et al., "Prostaglandin E Receptor Subtypes in Mouse Osteoblastic Cell Line," *Endocrinology*, 1996, pp. 1698–1705, 137, No. 5.

Suzawa, et al., "The Role of Prostaglandin E Receptor Subtypes (EP1, EP2, EP3, and EP4) in Bone Resorption: An Analysis Using Sepcific Agonists for the Respective EPs," *Endocrinology*, 2000, pp. 1554–1559, 141(4).

Ono, et al., Important role of $EP_4$, a subtype of prostaglandin (PG) E receptor, in osteoclast–like cell formation from mouse bone marrow cells induced by $PGE_2$, *Journal of Endocrinology*, 1998, pp. R1–R5, 158.

*Primary Examiner*—Paul J. Killos
(74) *Attorney, Agent, or Firm*—Robert C. Hall; Rohan Peries

(57) ABSTRACT

This invention relates to compounds which are generally $EP_4$ receptor agonists and which are represented by Formula I:

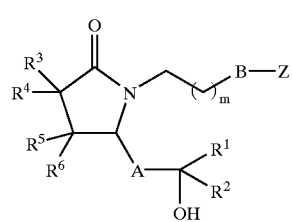

wherein A is a —$CH_2$—$CH_2$—, or —CH=CH—; B is absent, an aryl, or heteroaryl group; $R^1$ is alkyl, alkenyl, alkynyl, cycloalkylalkyl, heterocyclylalkyl, aryl, arylalkyl or heteroaryl, when B is aryl or heteroaryl and $R^3$, $R^4$, $R^5$ and $R^6$ are not simultaneously hydrogen, or $R^1$ is heterocyclylalkyl, aryl, or heteroaryl when B is absent and $R^3$, $R^4$, $R^5$ and $R^6$ are simultaneously hydrogen; and the other substituents are as defined in the specification; or individual isomers, racemic or non-racemic mixtures of isomers, or pharmaceutically acceptable salts or solvates thereof. The invention further relates to pharmaceutical compositions containing such compounds, methods for their use as therapeutic agents, and methods of preparation thereof.

29 Claims, No Drawings

8-AZA-11-DEOXY PROSTAGLANDIN ANALOGUES

CROSS-REFERENCE TO RELATED APPLICATION

This application claims the benefit under 35 U.S.C. 119(e) of priority of U.S. Provisional Patent Applications Ser. No. 60/305,727, filed Jul. 16, 2001 and Ser. No. 60/371,348, filed Apr. 10, 2002, the disclosure of which is herein incorporated by reference.

FIELD OF THE INVENTION

This invention relates to certain 8-aza-11-deoxy prostaglandin analogues, and associated pharmaceutical compositions, methods for use as selective prostaglandin $EP_4$ agonists, and methods of preparation thereof.

BACKGROUND OF THE INVENTION

There are many references in the literature to prostaglandins or prostanoids (PGs), a term which is generic to natural and synthetic prostaglandins and prostaglandin-like compounds, and it is well known that even slight differences in their chemical structures or stereochemical configurations will have profound effects on their biological activity.

Prostaglandins or prostanoids (PGs) are a group of bioactive compounds derived from membrane phospholipids, and are formed from 20-carbon essential fatty acids and a cyclopentane ring. They fall into several main classes designated by letters and are distinguished by substitutions to the cyclopentane ring. The main classes are further subdivided by subscripts 1, 2, or 3 which reflect their fatty acid precursors.

An example of a particular species of the prostaglandin E is $PGE_2$, with the following structure:

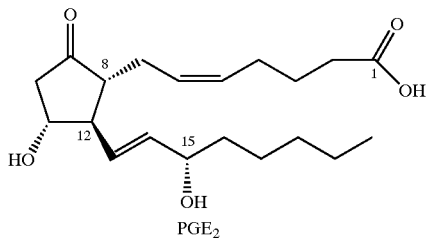

$PGE_2$

At present four different receptor subtypes of $PGE_2$ receptors are known and they are designated $EP_1$, $EP_2$, $EP_3$, and $EP_4$.

Uses for compounds possessing binding activity similar to $PGE_2$ comprise the prevention and/or treatment of immunological diseases (autoimmune diseases, organ transplantation, etc.), asthma, abnormal bone formation, neuronal cell death, thrombosis and stroke, hepatopathy, abortion, male and female sexual dysfunction, premature birth, inflammation such as rheumatoid arthritis, or retina neuropathy disorders such as glaucoma.

Prostaglandins and their associated receptors are more fully described in for example: M. Abramovitz et al., The Utilization of Recombinant Prostanoid Receptors to Determine the Affinities and Selectivities of Prostaglandins and Related Analogs, *Biochimica et Biophysica Acta* 2000, 1483, 285–293.

The involvement of prostaglandin E receptor agonists in bone resorption is described in, e.g., T. Suzawa et al., The Role of Prostaglandin E Receptor Subtypes in Bone Resorption: An Analysis Using Specific Agonists for the Respective EPs, *Endocrinology* 2000, 141, 1554–1559; K. Ono et al., Important Role of $EP_4$, a Subtype of Prostaglandin (PG) E Receptor, in Osteoclast-like Cell Formation from Mouse Bone Marrow Cells Induced by $PGE_2$, *J. of Endocrinology* 1998, 158, R1–R5; M. Suda et al., Prostaglandin E Receptor Subtypes in Mouse Osteoblastic Cell Line, *Endocrinology* 1996, 137, 1698–1705.

These selective prostaglandin E receptor agonists are also useful for the treatment of gastric lesions, see e.g. H. Araki, et al. The Roles of Prostaglandin E Receptor Subtypes in the Cytoprotective Action of Prostaglandin $E_2$ in Rat Stomach, *Aliment. Pharmacol. Ther.* 2000, 14 (Suppl. 1), 116–124; T. Kunikata, et al., E Type Prostaglandin Inhibits Indomethacin-Induced Small Intestinal Lesions Through $EP_3$ and $EP_4$ Receptors: A Study Using Rats and Knockout Mice, *Gastroenterology* 118, abstract #3787.

Other uses of prostaglandin E receptor agonists are for improvement of kidney function as described in, e.g., M. D. Breyer, et al, Prostaglandin E Receptors and the Kidney, *Am. J. Physiol.* 2000, 279, F12–F23, and K. E. Purdy, et al., $EP_1$ and $EP_4$ Receptors Mediate Prostaglandin $E_2$ Actions in the Microcirculation of Rat Kidney, *Am. J. Physiol.* 2000, 279, F755–F764; for thrombosis and stroke as well as for other conditions where an inhibition of platelet aggregation would be beneficial as described in, e.g., B. Z. S. Paul, et al, Distribution of Prostaglandin IP and EP Receptor Subtypes and Isoforms in Platelets and Human Umbilical Artery Smooth Muscle Cells, *Br. J. Haematol.* 1998, 102, 1204–1211; for antiinflammatory effects through inhibition of TNF-alpha generation as described in, e.g. K. K. Meja, et al. Characterization of prostanoid receptor(s) on human blood monocytes at which prostaglandin E2 inhibits lipopolysaccharide-induced tumor necrosis factor-alpha generation, *Br. J. Pharmacol.* 1997, 122, 149–157, and A. Eigler, et al. Anti-inflammatory activities of cAMP-elevating agents: enhancement of IL-10 synthesis and concurrent suppression of TNF production, *J. Leukoc. Biol.* 1998, 63, 101–107; or for glaucoma as described in, e.g., M. Takamatsu, et al. Localization of Prostaglandin E Receptor Subtypes in The Ciliary Body of Mouse Eye, *Exp. Eye Res.* 2000, 70, 623–628, and D. F. Woodward, et al, Molecular Characterization and Ocular Hypotensive Properties of the Prostanoid $EP_2$ Receptor, *J. Ocul. Pharmacol. Ther.* 1995, 11, 447.

Treatment of impotence and/or erectile dysfunction by using prostaglandins that are selective $EP_2$ and/or $EP_4$ receptor agonists have been disclosed in International Application Publication No. WO 99/02164 assigned to Pharmacia & Upjohn AB.

Additional information relating to prostaglandins and their receptors is described in *Goodman & Gillman's, The Pharmacological Basis of Therapeutics*, ninth edition, McGraw-Hill, New York, 1996, Chapter 26, pages 601–616.

8-Aza-11-deoxy-prostaglandin analogs corresponding to $PGE_2$ would have the following structure:

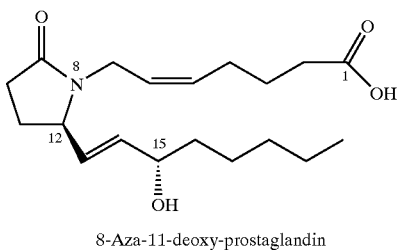

8-Aza-11-deoxy-prostaglandin

Substitution of a nitrogen for the carbon at C-8 causes a change in the three dimensional conformation of the resultant prostaglandin, and because structure is related to biological activity, such a conformational change will have a profound effect upon the biological activity. 8-Aza-11-deoxy prostaglandin E analogues with the natural side chains have been reported in the literature, see e.g. BE 841,165, assigned to Syntex USA, Inc.

Compounds of this invention are 8-azaprostaglandins with a non-natural side chain on the C-12 position of the pyrrolidone ring (following prostaglandin nomenclature), said chain containing a heterocyclyl, an aryl or a heteroaryl ring at the C-15 position of the chain. These compounds have high selectivity in their $EP_4$ receptor agonist activity. The increase in selectivity would alleviate the severe side effects frequently observed following administration of non-selective prostaglandins agonists. Therefore compounds of this invention are desirable.

SUMMARY OF THE INVENTION

This invention relates to compounds comprising Formula I:

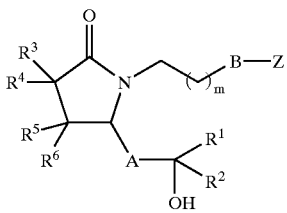

wherein:
A is —$CH_2$—$CH_2$—, or —CH=CH—;
B is absent, aryl, or heteroaryl;
Z is —C(O)OR', —C(O)NR'R", —C(O)$NSO_2$R', —PR'(O)(OR'), —PO(OR')$_2$, or tetrazol-5-yl;
wherein R' and R" are independently from each other hydrogen or ($C_1$–$C_6$)alkyl;
m is 1, 2, 3, 4, 5, or 6;
$R^1$ is alkyl, alkenyl, alkynyl, cycloalkylalkyl, heterocyclylalkyl, aryl, arylalkyl or heteroaryl;
provided that $R^1$ is alkyl, alkenyl, alkynyl, cycloalkylalkyl, heterocyclylalkyl, aryl, arylalkyl or heteroaryl, when B is aryl or heteroaryl and $R^3$, $R^4$, $R^5$ and $R^6$ are not simultaneously hydrogen, and
$R^1$ is heterocyclylalkyl, aryl, or heteroaryl, when B is absent and $R^3$, $R^4$, $R^5$ and $R^6$ are simultaneously hydrogen;
$R^2$ is hydrogen or ($C_1$–$C_6$)alkyl, ($C_1$–$C_6$)alkenyl, or ($C_1$–$C_6$)alkynyl;
$R^3$, $R^4$, $R^5$ and $R^6$ are each independently from each other hydrogen or ($C_1$–$C_6$) alkyl; or $R^3$ and $R^4$, $R^5$ and $R^6$ or $R^3$ and $R^5$ taken together with the atom to which they are attached may form a ($C_3$–$C_7$) alkyl ring; or a pharmaceutically acceptable salt or solvate, single isomer or racemic or non-racemic mixture of isomers thereof.

In another aspect the invention relates to pharmaceutical compositions containing a therapeutically effective amount of at least one compound of Formula I or its pharmaceutically acceptable salt or solvate, prodrug, single isomer or racemic or non-racemic mixture of isomers in admixture with at least one suitable carrier, diluent or excipient.

In another aspect the invention provides a method of treatment of a disease, in particular a bone disease, in a mammal treatable by administration of a prostaglandin $EP_4$ receptor agonist, comprising administration of a therapeutically effective amount of a compound of Formula I or its pharmaceutically acceptable salt.

In another aspect the invention provides a process for preparing compounds of Formula I.

DEFINITIONS

Unless otherwise stated, the following terms used in the specification and claims have the meanings given below:

"Alkoxy" means a radical —OR where R is an alkyl as defined herein e.g., methoxy, ethoxy, propoxy, butoxy and the like.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylthio" or "alkylsulfanyl" means a radical —SR where R is an alkyl as defined above e.g., methylthio, ethylthio, propylthio, butylthio, and the like.

"Aryl" means a monovalent monocyclic or bicyclic aromatic hydrocarbon radical which is optionally substituted independently from each other with one or more substituents, preferably one, two, or three, selected from the group consisting of alkyl, haloalkyl, halo, nitro, cyano, amino, methylenedioxy, ethylenedioxy, Y-aryl, Y-heteroaryl, Y-cycloalkyl, —Y-heterocyclyl, —Y—OR', —Y—NR'R", —Y—C(O)—R', —Y—S(O)$_{0-2}$—R'; —Y—N—$SO_2$—R', —Y—$SO_2$—NR'R", —Y—N—C(O)—NR'R", where Y is absent or a $C_1$–$C_3$ alkylene group, and R' and R" are each independently from each other hydrogen, alkyl, haloalkyl, hydroxy, alkoxy, aryl, heteroaryl, cycloalkyl, heterocyclyl. More specifically the term aryl includes, but is not limited to, phenyl, chlorophenyl, methoxyphenyl, methoxymethylphenyl, phenyloxyphenyl, 1-naphthyl, 2-naphthyl, and the derivatives thereof.

"Cycloalkyl" refers to a saturated monovalent cyclic hydrocarbon radical of three to seven ring carbons e.g., cyclopropyl, cyclobutyl, cyclohexyl, 4-methyl-cyclohexyl, and the like.

"Halo" means fluoro, chloro, bromo, or iodo, preferably fluoro and chloro.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently from each other with one or more substituents, preferably one or two substituents, selected from alkyl, haloalkyl, halo, nitro, cyano, amino, methylenedioxy, Y-aryl, Y-heteroaryl, Y-cycloalkyl, —Y-heterocyclyl, —Y—OR', —YNR'R", —Y—C(O)—R', —Y—O—C(O)—R', —Y—S(O)$_{0-2}$—R'; —Y—N—SO$_2$—R', —Y—SO$_2$—NR'R", —Y—N—C(O)—N—R'R", where Y is absent or a C$_1$–C$_3$ alkylene group and R' and R" are each independently from each other hydrogen, alkyl, haloalkyl, hydroxy, alkoxy, aryl, heteroaryl, cycloalkyl, heterocyclyl. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

"Heterocyclyl" means a saturated or unsaturated non-aromatic cyclic radical of 3 to 8 ring atoms in which one or two ring atoms are heteroatoms selected from N, O, or S(O)$_{0-2}$, the remaining ring atoms being C, where one or two C atoms may optionally be replaced by a carbonyl group. The heterocyclyl ring may be optionally substituted independently from each other with one, two, or three substituents selected from alkyl, haloalkyl, halo, nitro, cyano, —Y-aryl, Y-heteroaryl, Y-cycloalkyl, —Y-heterocyclyl, —Y—OR', —YNR'R", —Y—C(O)—R', —Y—S(O)$_{0-2}$—R'; —Y—N—SO$_2$—R', —Y—SO$_2$—NR'R", —Y—N—C(O)—N—R'R", where Y is absent or a C$_1$–C$_3$ alkylene group and R' and R" are each independently from each other hydrogen, alkyl, haloalkyl, hydroxy, alkoxy, aryl, heteroaryl, cycloalkyl, heterocyclyl. More specifically the term heterocyclyl includes, but is not limited to, tetrahydropyranyl, piperidinyl, N-methylpiperidin-3-yl, piperazinyl, N-methylpyrrolidin-3-yl, 3-pyrrolidinyl, morpholinyl, thiomorpholinyl, thiomorpholino-1-oxide, thiomorpholino-1,1-dioxide, pyrrolinyl, imidazolinyl, N-methanesulfonyl-piperidin-4-yl, and the derivatives thereof.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted phenyl" means a phenyl ring which is optionally substituted independently from each other with one or more substituents, preferably one or two substituents selected from the group consisting of alkyl, hydroxy, alkoxy, haloalkyl, haloalkoxy, heteroalkyl, halo, nitro, cyano, amino, methylenedioxy, ethylenedioxy, and acyl.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J., *Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Atropic isomers" means the isomers owing their existence to restricted rotation caused by hindrance of rotation of large groups about a central bond.

The compounds of this invention may exist in stereoisomeric form, therefore can be produced as individual stereoisomers or as mixtures.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same acid addition salt.

"Crystal forms" (or polymorphs) means crystal structures in which a compound can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1–92, Elesevier, New York-Oxford (1985).

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2$^{nd}$ ed. 1991) and Harrison and Harrison et al., *Compendium of Synthetic Organic Methods*, Vols. 1–8 (John Wiley and Sons, 1971–1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Prostaglandin analog" is a non-naturally-occurring compound which is structurally similar to a prostaglandin.

"Prostaglandin receptor" or "prostanoid receptor" is a naturally-occurring protein that binds prostaglandins, which when bound alters the function of a cell. Prostaglandin receptors may be characterized as either excitatory or relaxant. Such receptors include but are not limited to $EP_1$, $EP_2$, $EP_3$, $EP_4$, DP, FP, IP, $TP_1$, and $TP_2$. These receptors are further discussed by Coleman et al, in *Pharmacological Reviews*, 1994, Volume 6, No. 2, pages 205–229.

ABBREVIATIONS

Throughout the application the following abbreviations are used with the following meanings:

| | |
|---|---|
| DME | Ethylene glycol dimethyl ether |
| DMF | Dimethylformamide |
| DMSO | Dimethylsulfoxide |
| EtOAc | Ethyl acetate |
| MS | Mass Spectrum |
| THF | Tetrahydrofuran |
| rt | Room (ambient) temperature |

NOMENCLATURE

The naming and numbering of the compounds of this invention is illustrated below:

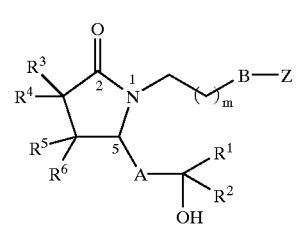

In general, the nomenclature used in this Application is based on AUTONOM™ v.4.0 a Beilstein Institute computerized system for the generation of IUPAC systematic nomenclature.

For example a compound of Formula I wherein Z is —C(O)OH; m is 5; $R^2$, $R^3$, $R^4$, $R^5$, and $R^6$ are hydrogen; A is —$CH_2$=$CH_2$—; B is absent, and $R^1$ is phenyl is named 7-[(R)-2-((E)-3-hydroxy-3-phenyl-propenyl)-5-oxo-pyrrolidin-1-yl]-heptanoic acid.

PREFERRED EMBODIMENTS

While the broadest definition of this invention is set forth in the Summary of the Invention, certain compounds of Formula I are preferred.

In a first embodiment, a representative group of compounds is one wherein B is absent, $R^1$ is aryl; A, $R^2$, $R^3$, $R^4$, $R^5$, $R^6$ and Z are as defined above. A preferred group of compounds within this embodiment are those wherein $R^1$ is an aryl optionally substituted with a substituent selected from trifluoromethyl, halogen, —Y—$R^a$, —Y—$OR^a$ and —Y—C(O)$R^a$, wherein Y is a bond or a ($C_1$–$C_3$)alkylene group, and $R^a$ is hydrogen, ($C_1$–$C_6$)alkyl, aryl, heterocyclyl, heteroaryl or heterocyclyl. Preferably, $R^1$ is an aryl optionally substituted with a substituent selected from —Y—$R^a$, —Y—$OR^a$, and —Y—C(O)$R^a$, wherein Y is a bond or a ($C_1$–$C_3$)alkylene group, and $R^a$ is an unsubstituted phenyl or a substituted phenyl with at least one substituent selected from ($C_1$–$C_6$)alkyl, ($C_1$–$C_6$)alkoxy, trifluoromethyl, or halogen.

In a second embodiment of Formula I, B is absent, A, $R^2$, $R^3$, $R^4$, $R^5$, $R^6$ and Z are as defined above and $R^1$ is a phenyl group substituted with —Y—$R^a$, wherein Y is a bond or a ($C_1$–$C_3$)alkylene group, and $R^a$ is a phenyl optionally substituted with a substituent selected from ($C_1$–$C_6$)alkyl, ($C_1$–$C_6$)alkoxy, trifluoromethyl, or halogen. Preferably, $R^1$ is a phenyl group substituted with at least one —Y—$OR^a$, wherein Y is a bond or a ($C_1$–$C_3$)alkylene group, and $R^a$ is a phenyl optionally substituted with an ($C_1$–$C_6$)alkyl, an ($C_1$–$C_6$)alkoxy, a trifluoromethyl, or a halogen. More preferably, $R^1$ is a phenyl group substituted with a —Y—C(O)$R^a$, wherein Y is a bond or a ($C_1$–$C_3$)alkylene group, and $R^a$ is a phenyl optionally substituted with a substituent selected from ($C_1$–$C_6$)alkyl, ($C_1$–$C_6$)alkoxy, trifluoromethyl or halogen.

In a third embodiment are compounds of Formula I wherein B is absent, A is —CH=CH—, $R^2$, $R^3$, $R^4$, $R^5$, $R^6$ and Z are as defined above and $R^1$ is heteroaryl. Representative compounds are those wherein the heteroaryl group is substituted with a group selected from trifluoromethyl, halogen; —Y—$R^a$, —Y—$OR^a$ and —Y—C(O)$R^a$, wherein Y is a bond or a ($C_1$–$C_3$)alkylene group, and $R^a$ is ($C_1$–$C_6$)alkyl, aryl, heterocyclyl, heteroaryl or heterocyclyl.

In a fourth embodiment are compounds of Formula I wherein B is absent, A is —$CH_2$—$CH_2$—, $R^2$, $R^3$, $R^4$, $R^5$, $R^6$ and Z are as defined above and $R^1$ is heteroaryl. Representative compounds are those wherein the heteroaryl group is substituted with a group selected from trifluoromethyl, halogen; —Y—$R^a$, —Y—$OR^a$ and —Y—C(O)$R^a$, wherein Y is a bond or a ($C_1$–$C_3$)alkylene group, and $R^a$ is ($C_1$–$C_6$)alkyl, aryl, heterocyclyl, heteroaryl or heterocyclyl.

In a fifth embodiment are compounds of Formula I wherein B is absent, $R^3$ and $R^4$ are ($C_1$–$C_6$)alkyl; $R^2$, $R^5$, $R^6$ and Z are as defined above, A is —$CH_2$—$CH_2$— and $R^1$ is a phenyl, heteroaryl, an alkyl or a cycloalkylalkyl group. Preferably $R^1$ is a phenyl substituted with at least one group selected from trifluoromethyl, halogen, —Y—$R^a$, —Y—$OR^a$ and —Y—C(O)$R^a$, wherein Y is a bond or a ($C_1$–$C_3$)alkylene group, and $R^a$ is ($C_1$–$C_6$)alkyl, aryl, heterocyclyl, heteroaryl or heterocyclyl. More preferably $R^1$ is a heteroaryl substituted with at least one group selected from trifluoromethyl, halogen, —Y—$R^a$, —Y—$OR^a$ and —Y—C(O)$R^a$, wherein Y is a bond or a ($C_1$–$C_3$)alkylene group, and $R^a$ is ($C_1$–$C_6$)alkyl, aryl, heterocyclyl, heteroaryl or heterocyclyl. Still more preferably, $R^1$ is an alkyl or a cycloalkylalkyl group.

In a sixth embodiment, B is absent, $R^2$, $R^3$, $R^4$, $R^5$, $R^6$ and Z are as defined above, A is —CH=CH—, $R^1$ is a phenyl optionally substituted with a substituent selected from trifluoromethyl, halogen, —Y—$R^a$, —Y—$OR^a$ and —Y—C(O)$R^a$, wherein Y is a bond or a ($C_1$–$C_3$)alkylene group, and $R^a$ is ($C_1$–$C_6$)alkyl, aryl, heterocyclyl, heteroaryl or heterocyclyl.

In a seventh embodiment, B is absent, $R^2$, $R^3$, $R^4$, $R^5$, $R^6$ and Z are as defined above, A is —$CH_2$—$CH_2$—, $R^1$ is a phenyl optionally substituted with a substituent selected from trifluoromethyl, halogen, —Y—$R^a$, —Y—$OR^a$ and Y—C(O)$R^a$, wherein Y is a bond or a ($C_1$–$C_3$)alkylene group, and $R^a$ is ($C_1$–$C_6$)alkyl, aryl, heterocyclyl, heteroaryl or heterocyclyl.

In an eighth embodiment, B is an aryl, m is one or two, $R^2$, $R^3$, $R^4$, $R^5$, $R^6$, A and Z are as defined above, and $R^1$ is an alkyl or aryl optionally substituted with a substituent selected from trifluoromethyl, halogen, —Y—$R^a$, —Y—$OR^a$ and —Y—C(O)$R^a$, wherein Y is a bond or a ($C_1$–$C_3$)alkylene group, and $R^a$ is ($C_1$–$C_6$)alkyl, aryl, heterocyclyl, heteroaryl or heterocyclyl. Preferably, $R^1$ is an optionally substituted phenyl.

In a ninth embodiment, B is heteroaryl, m is one or two and $R^1$ is an alkyl, m is one or two, $R^2$, $R^3$, $R^4$, $R^5$, $R^6$, A and Z are as defined above. Preferred compounds within this embodiment are those wherein A is —CH=CH—.

The structure of the compounds of Formula I may include optical isomers, diastereomers, enantiomers of the above structure or pharmaceutically-acceptable salts, biohydrolyzable amides, esters, or imides thereof. Preferred stereochemistry mimics that of naturally occurring $PGE_2$.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formula I are capable of further forming pharmaceutically acceptable base addition salts. All of these forms are within the scope of the present invention.

General Synthetic Scheme

The compounds of this invention can be made by the methods depicted in the reaction schemes shown below. One skilled in the art will understand that certain modifications to the schemes are within the scope of the present invention as, for example certain steps involving the use of protecting groups for functional groups that are not compatible with particular reaction conditions.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art. These schemes are merely illustrative of some methods by which the compounds of this invention can be synthesized, and various modifications to these schemes can be made and will be suggested to one skilled in the art having referred to this disclosure.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Scheme A below describes a general method of preparing compounds of Formula I and its analogs. In general, these compounds are prepared by reacting a phosphonate of formula m with an aldehyde of formula a to yield a compound of formula b.

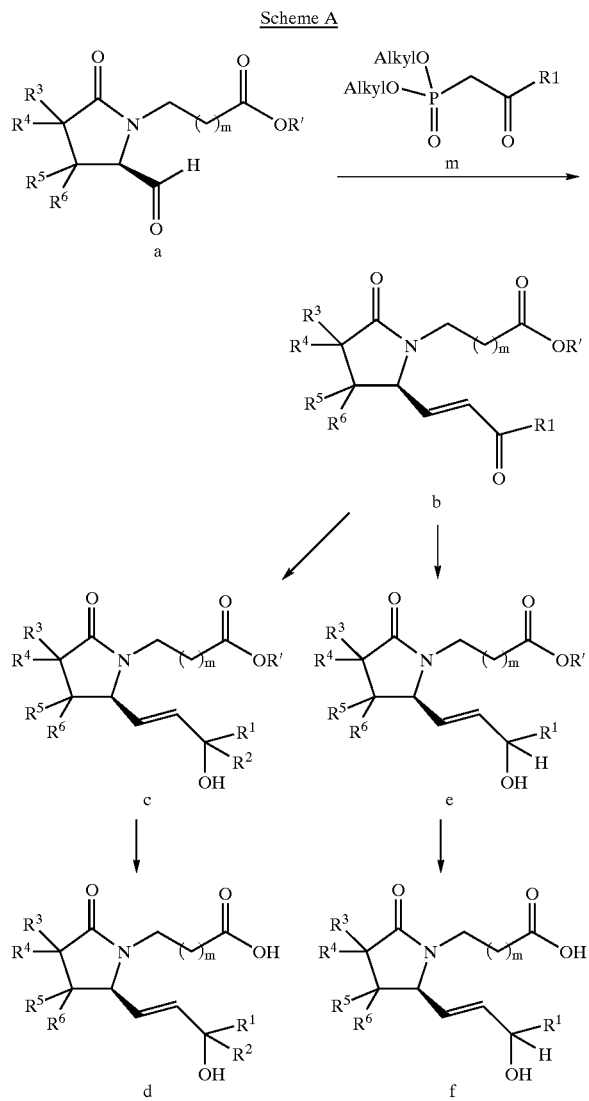

Aldehydes of formula a (wherein R' is methyl, B is absent, m is five, $R^3$, $R^4$, $R^5$ and $R^6$ are hydrogen, the recited radicals correponding to those in Formula I) are known in the art. For example, (R)-5-(hydroxymethyl)-2-pyrrolidinone is a commercial product and its preparation and conversion to a are described in S. Saijo et al., Chem. Pharm. Bull. 1980, 28, 1449–1458; (R)-3,3-dimethyl-5-(hydroxymethyl)-2-pyrrolidinone, wherein $R^3$ and $R^4$ are methyl and $R^5$ and $R^6$ are hydrogen, can be prepared according to Y. Nakagawa, et al., Tetrahedron 1998, 54, 10295–10307; and 4,4-dimethyl-5-(hydroxymethyl)-2-pyrrolidinone, wherein $R^3$ and $R^4$ are hydrogen and $R^5$ and $R^6$ are methyl can be prepared according to R. L. Mackman, et al., J. Chem. Soc., Perkin Trans., 1997, 2111–2122.

Reaction of aldehyde a with a β-ketophosphonate, of general formula m in the presence of a base such as, for example, sodium hydride, potassium t-butoxide, potassium hexamethyldisilazide, or lithium chloride with a tertiary amine, in a solvent such as acetonitrile, tetrahydrofuran, 1,2-dimethoxyethane, or t-butylmethylether, yields a compound of formula b, wherein —CH=CH— corresponds to A in Formula I.

Simple reduction of the ketone b with a hydride such as for example zinc borohydride in a solvent such as dichloromethane, toluene, ethanol, or tetrahydrofuran or the combination of sodium borohydride-cerium (III) chloride in a protic solvent such as methanol yields a diasteromeric mixture of alcohols of formula e.

To obtain a compound of Formula I wherein A is —$CH_2$—$CH_2$—, and $R^1$ is aryl or heteroaryl, the double bond in compound b is initially reduced under an atmosphere of hydrogen gas in the presence of a catalyst such as platium oxide or palladium on carbon. Other hydride reagents that can be use are, for example, the stoichiometric combination of lithium aluminum hydride-ethanol-(R)-(–)-binaphthol as described by R. Noyori, et al., J. Am. Chem. Soc. 1984, 106, 6717–6725; the combination of catalytic amounts of (S)-2-methyl-"CBS"-oxazaborolidine with stoichiometric borane-dimethyl sulfide as described by E. J. Corey, et al., J. Am. Chem. Soc. 1987, 109, 7925–7926; or stoichiometric amounts of (S)-3-pinanyl-9-borabicyclo[3.3.1]nonane as described by M. M. Midland et al., J. Am. Chem. Soc. 1980, 102, 867–869 to obtain compound c.

Alternatively, the saturated alcohol (i.e., related to compounds of the general structure e of Scheme A) of the general Formula I (when radical $R^1$ aryl or heteroaryl) can be obtained directly from compounds of formula b by exposure to sodium borohydride in a protic solvent as ethanol or 2-methoxyethanol.

Compounds of general formula d are prepared by the reaction of compounds of formula b and c with an organomagnesium halide comprising the $R^2$ as defined above for Formula I, more preferably, with a Grignard reagent of general formula $R^2MgBr$.

The esters c and e are hydrolyzed to the corresponding acids d and f by procedures well known by the artisan, such as addition of a base such as lithium, sodium of potassium hydroxyde, or an acid such as sulfuric acid or hydrochloric acid in a protic or ethereal solvent containing water, or by employing a Lipase type VII in 0.05 M aqueous phosphate buffer at pH 6.8 as described by C. Luthy, et al. J. Am. Chem. Soc. 1978, 100, 6211–6217.

The phosphonate of general formula m can be prepared according to a method described in Scheme B below.

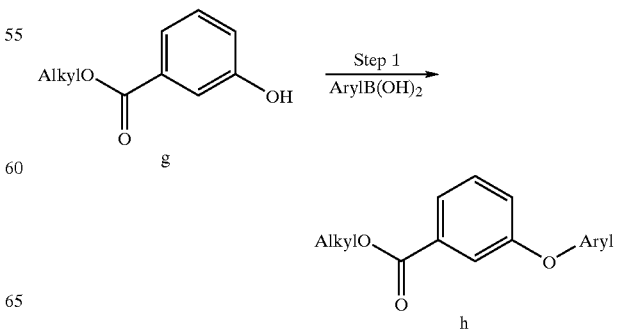

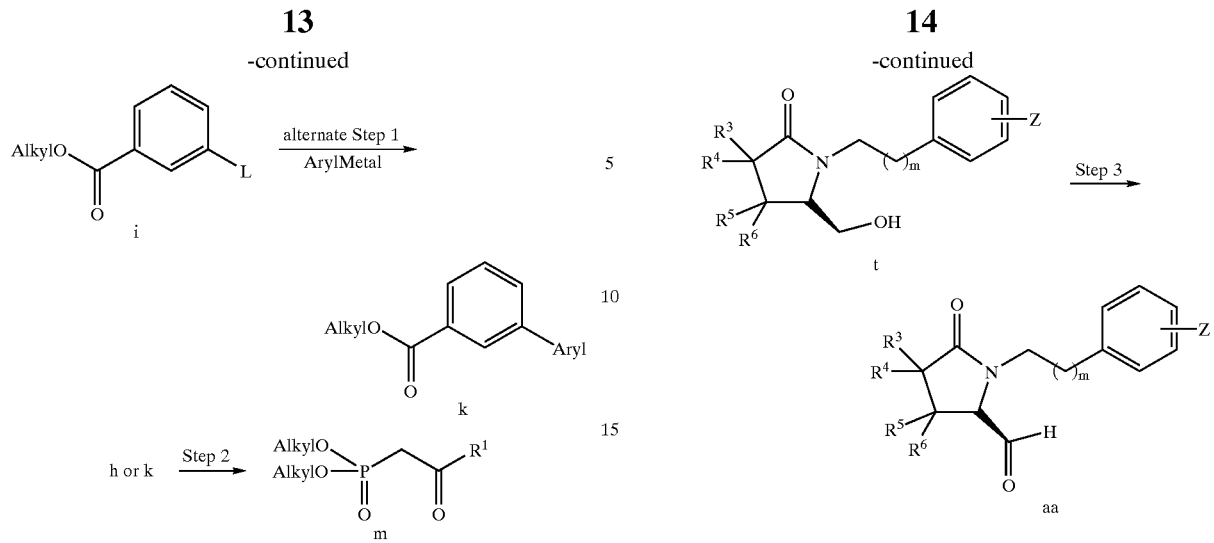

Benzoic acid derivatives, for example, compounds of formula g and j, (wherein L is a leaving group as defined herein) are either readily available or easily synthesized by those of ordinary skill in the art and are converted to compounds of formula h and k, respectively. The conditions for the preparation of compounds of formula h are described in D. A. Evans et al. *Tetrahedron Lett.* 1998, 39, 2937. The methods for the preparation of compounds of formula k are described in A. M. Echavarren and J. K. Stille *J. Am. Chem. Soc.* 1987, 109, 5478–5486, N. Miyaura and A. Suzuki *Chem. Rev.* 1995, 95, 2457–2483, and A. F. Littke et al. *J. Am. Chem. Soc.* 2000, 122, 4020–4028. Compounds h and k are converted into compound m by exposure to dialkyl methyl phosphonate, which is initially treated with a base such as normal butyllithium or lithium diisopropylamide in an inert ether solvent such as tetrahydrofuran, or t-butylmethyl ether.

Scheme C describes a general method of synthesizing compounds of Formula I, wherein B is aryl or a heteroaryl.

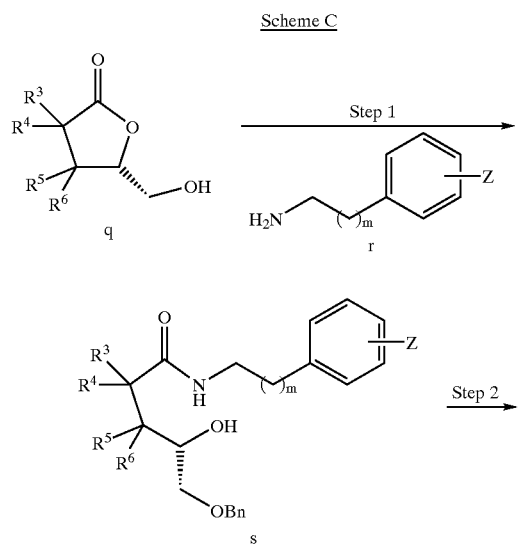

Compounds of the formula q are known. For example, furanone, a compound of formula q, wherein $R^3$, $R^4$, $R^5$ and $R^6$ are hydrogen is a commercial product. Compounds of formula r are also known. For example, phenethyl amine, when Z in r is p-C(O)OH and m is 1, is a commercial product and can be converted into the corresponding ester by a person of ordinary skill in the art.

In Scheme C step 1, the hydroxyl of compound q is first protected with a protecting group as described in the specification, for example benzyl group. The protected lactone q is condensed with amine r, neat or in a polar solvent such as acetonitrile, N-methyl-2-pyrrolidinone, isopropanol, or tetrahydrofuran to obtain compound s. Compounds of the formula t are prepared by activating the primary hydroxyl group of structure s (to a leaving group) by treatment with benzene sulfonyl chloride or methanesulfonyl chloride. The lactam formation is accomplished by exposure to a base such as potassium t-butoxide, sodium methoxide, or the like. Deprotection of the primary hydroxyl by reduction, with for example, hydrogen gas with a catalyst such as Raney-Ni, platinum oxide, or palladium on carbon will furnish compounds of the general structure t. Compound t is converted into aldehyde aa by methods known in the art. Aldehyde aa is converted into a compound of invention by the method described in Scheme A above for the conversion of aldehyde a.

Utility

The compounds of the present invention are selective $EP_4$ prostaglandin agonists and may be used to treat several disease states associated with prostaglandin $EP_4$ receptor-mediated diseases, particularly for disease states associated with bone disorders, characterized by low bone mass and deterioration of bone tissue, with a consequent increase in bone fragility and susceptibility to fracture, especially those that require a significant increase in bone mass, bone volume, or bone strength. Conditions associated with low bone mass refer to a condition where the level of bone mass is below the age specific normal. Childhood idiopathic and primary osteoporosis are also included. Included in the treatment of osteoporosis is the prevention or attenuation of long term complications such as curvature of the spine, loss of height, prosthetic surgery, fracture healing and prevention of prostate malfunctioning. Also included is the treatment of bone loss associated with periodontitits or prosthetic ingrowth. Those skilled in the art will recognize that the term bone mass actually refers to bone mass per unit area which is sometimes referred to as bone mineral density. It has been discovered that the 8-aza-11-deoxy prostaglandin analogs of the present invention are useful for treating bone disorders.

Other uses of these compounds comprise prevention and/or treatment of allergy, alveolar abscess, Alzheimer's disease, Amyotrophic lateral sclerosis (ALS), arthritis, asthma, atopy, bronchitis, burns, cancer, cardiovascular disease, Crohn's disease, chronic obstructive respiratory diseases, congestive heart failure, gingivitis, glomerulonephritis, hepatitis, hepatic injury, acute hepatitis, hypertension, hypercytokinemia, immune disorders, inflammatory bowel disease, Kawasaki disease, liver failure, liver disease, lung failure, macrophage activation syndrome, multiorgan failure, multiple sclerosis, myocardial ischemia, nephritis, neurodegeneration, neuronal death, organ transplant rejection, periodontitis, platelet aggregation, pulmonary injury, pulmonay fibrosis, pulmonary emphysema, renal failure, renal insufficiency, renal disorders, respiratory disease, septicemia, sepsis, shock, sleep and platelet aggregation disorders, Still disease, systemic granuloma, thrombosis, ulcerative colitis and uremia or as osteogenesis promotor.

Testing

The compounds of the present invention of Formula I bind and act on $EP_4$ receptors which is a subtype of $PGE_2$ receptor. The effects of the compounds of the present invention may be measured with the activity assay using cells expressing prostanoid receptor subtypes as described in more detail in Example 10. The competitive binding activity of these compounds to the intended target may be measured as described in Example 11. The compounds of this invention may be evaluated for their effect on bone mass density in accord with the procedures of Gunness-Hey and Hock, *Metab. Bone Dis.* 5, 177–181 (1984), as described in more detail in Example 12.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula I may range from approximately 0.00005–10 mg per kilogram body weight of the recipient per day; preferably about 0.0001–1 mg/kg/day. Thus, for administration to a 70 kg person, the dosage range would preferably be about 0.01 mg to 1.0 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula I based on the total formulation, with the balance being one or more suitable pharmaceutical excipients. Preferably, the compound is present at a level of about 1–80 wt %. Representative pharmaceutical formulations containing a compound of Formula I are described in Example 9.

EXAMPLES

The following preparations and examples are given to enable those skilled in the art to more clearly understand and to practice the present invention. They should not be considered as limiting the scope of the invention, but merely as being illustrative and representative thereof.

Example 1

7-{(R)-2-[(E)-3-(3-Benzyl-phenyl)-3-hydroxy-propenyl]-5-oxo-pyrrolidin-1-yl}-heptanoic Acid

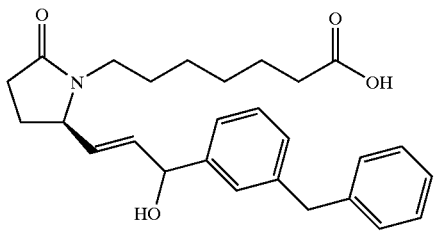

Step 1:

3-Benzyl-benzoic Acid Methyl Ester

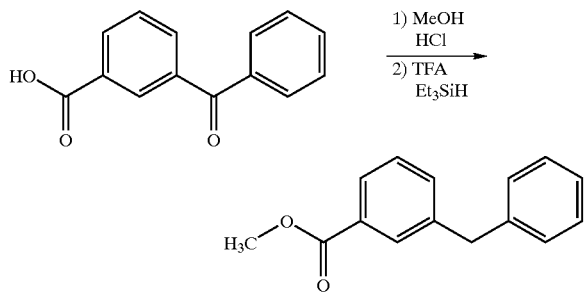

3-Benzoyl-benzoic acid (5.12 g, 22.6 mmol) was stirred in methanol (45 mL) with conc. $H_2SO_4$ (2.0 mL) for 18 h at 60° C. The reaction mixture was diluted with ethyl acetate and then washed with an aqueous $NaHCO_3$ solution. The organic layer was dried over $MgSO_4$, filtered, and concentrated to provide 3-benzoyl-benzoic acid methyl ester (5.4 g, 22.6 mmol) in quantitative yield as a yellow oil.

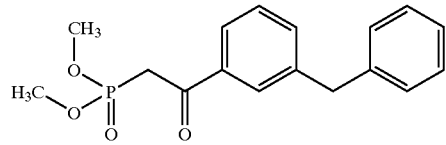

3-benzoyl-benzoic acid methyl ester (653 mg, 2.72 mmol) was stirred in trifluoroacetic acid (3 mL) with triethylsilane (1.3 mL, 8.15 mmol) at room temperature for 22 h. The reaction mixture was diluted with ethyl acetate and washed with an aqueous $NaHCO_3$ solution. The organic layer was dried over $MgSO_4$, filtered and concentrated. The resultant oil was subjected to column chromatography (25 hexanes: 1 ethyl acetate) to provide 3-benzyl-benzoic acid methyl ester (589 mg, 2.6 mmol) as an oil.

Step 2:

[2-(3-Benzoyl-phenyl)-2-oxo-ethyl]-phosphonic Acid Dimethyl Ester

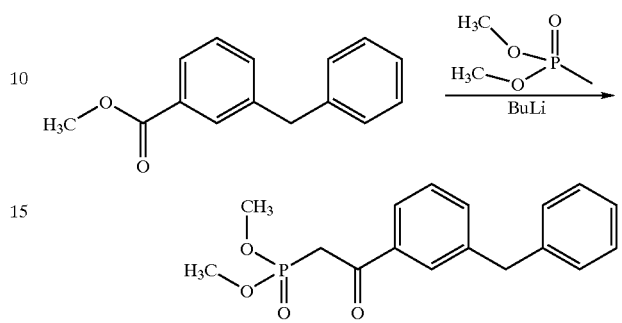

To a −78° C. THF solution (10 mL) of dimethylmethylphosphonate (0.423 mL, 3.9 mmol) was added 1.6M BuLi in hexanes (2.44 mL, 3.9 mmol). After 1 h a THF solution (5 mL) of 3-benzyl-benzoic acid methyl ester (589 mg, 2.6 mmol) was added. After 15 min. the reaction mixture was warmed to room temperature and stirred an additional 3 h. The reaction mixture was quenched with an aqueous $NaHCO_3$ solution and extracted with ethyl acetate. The organic layer was dried over $MgSO_4$, filtered and concentrated. The residue was subjected to column chromatography (18 ethyl acetate: 1 hexanes) to provide [2-(3-benzyl-phenyl)-2-oxo-ethyl]-phosphonic acid dimethyl ester (677 mg, 2.12 mmol) as an oil.

Step 3:

7-{(R)-2-[(E)-3-(3-Benzyl-phenyl)-3-oxo-propenyl]-5-oxo-pyrrolidin-1-yl}-heptanoic Acid Ethyl

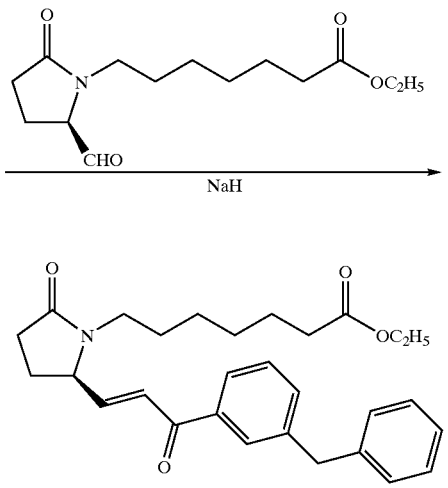

To 60% sodium hydride in mineral oil (20 mg, 0.51 mmol) was added a DME solution (5 mL) of [2-(3-benzyl-phenyl)-2-oxo-ethyl]-phosphonic acid dimethyl ester (164 mg, 0.51 mmol). After 1.5 h a DME solution (5 mL) of 7-((R)-2-formyl-5-oxo-pyrrolidin-1-yl)-heptanoic acid ethyl ester (126 mg, 0.47 mmol) was added. The reaction mixture was stirred for 45 min. at room temperature then diluted with ethyl acetate and washed with an aqueous $NaHCO_3$ solution.

The organic layer was dried over MgSO$_4$, filtered and concentrated. The residue was subjected to column chromatography (2.5 ethyl acetate: 1 hexanes) to provide 7-{(R)-2-[(E)-3-(3-benzyl-phenyl)-3-hydroxy-propenyl]-5-oxo-pyrrolidin-1-yl}-heptanoic acid ethyl ester (112 mg, 0.24 mmol) as an oil.

Step 4:

7-{(R)-2-[(E)-3-(3-Benzyl-phenyl)-3-hydroxy-propenyl]-5-oxo-pyrrolidin-1-yl}-heptanoic Acid

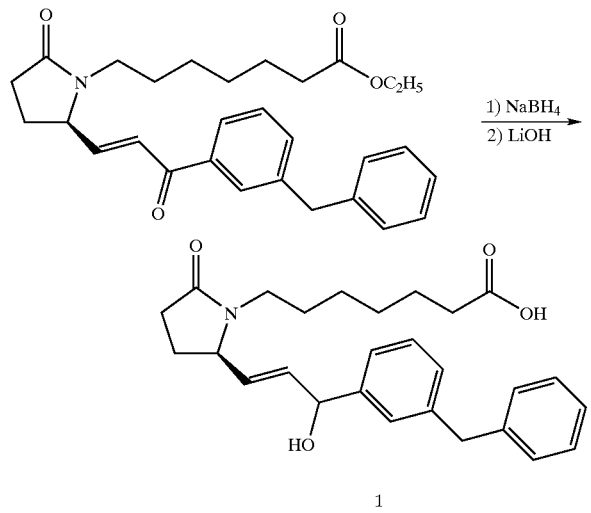

To an ethanol solution (5 mL) of 7-{(R)-2-[(E)-3-(3-Benzyl-phenyl)-3-hydroxy-propenyl]-5-oxo-pyrrolidin-1-yl}-heptanoic acid ethyl ester (112 mg, 0.24 mmol) was added NaBH$_4$ (37 mg, 0.97 mmol). The reaction mixture was stirred at room temperature for 2 h and then concentrated to near dryness. The residue was dissolved in ethyl acetate and washed with a brine solution. The organic layer was dried over MgSO$_4$, filtered and concentrated to provide 7-{(R)-2-[(E)-3-(3-benzyl-phenyl)-3-hydroxy-propenyl]-5-oxo-pyrrolidin-1-yl}-heptanoic acid ethyl ester (122 mg, 0.24 mmol) as an oil in quantitative yield. Subsequently it was dissolved in alcohol (5 mL), and an aqueous solution (2.5 mL) of lithium hydroxide monohydrate (44 mg, 1.05 mmol) was added. After stirring at room temperature for 4 h the reaction mixture was concentrated to near dryness. The resultant concentrated solution was diluted with brine and washed with dichloromethane. The aqueous layer was acidified with 1N HCl and the product extracted into dichloromethane. The organic layer was dried over MgSO$_4$, filtered and concentrated to provide 7-{(R)-2-[(E)-3-(3-benzyl-phenyl)-3-hydroxy-propenyl]-5-oxo-pyrrolidin-1-yl}-heptanoic acid (1) (77 mg, 0.18 mmol) as an oil. MS: 436 [(M+H)$^+$].

Following the method of Example 1 and replacing [2-(3-benzyl-phenyl)-2-oxo-ethyl]-phosphonic acid dimethyl ester in Step 3 with the following appropriate phosphonates prepared from the corresponding known acids or methyl esters as described in steps 1 and/or 2, the following compounds of Formula I were prepared:

(2-Naphthalen-2-yl-2-oxo-ethyl)-phosphonic acid dimethyl ester gives 7-[(R)-2-((E)-3-hydroxy-3-naphthalen-2-yl-propenyl)-5-oxo-pyrrolidin-1-yl]-heptanoic acid (2) MS: 396 [(M+H)$^+$];

[2-Oxo-2-(3-phenoxy-phenyl)-ethyl]-phosphonic acid dimethyl ester gives 7-{(R)-2-[(E)-3-hydroxy-3-(3-phenoxy-phenyl)-propenyl]-5-oxo-pyrrolidin-1-yl}-heptanoic acid (3) MS: 438 [(M+H)$^+$];

(2-Oxo-2-phenyl-ethyl)-phosphonic acid dimethyl ester gives 7-[(R)-2-((E)-3-hydroxy-3-phenyl-propenyl)-5-oxo-pyrrolidin-1-yl]-heptanoic acid (4) MS: 346 [(M+H)$^+$];

[2-(3-Methoxy-phenyl)-2-oxo-ethyl]-phosphonic acid dimethyl ester gives 7-{(R)-2-[(E)-3-hydroxy-3-(3-methoxy-phenyl)-propenyl]-5-oxo-pyrrolidin-1-yl}-heptanoic acid (5) MS: 376 [(M+H)$^+$];

[2-Oxo-2-(4-phenoxy-phenyl)-ethyl]-phosphonic acid dimethyl ester gives 7-{(R)-2-[(E)-3-hydroxy-3-(4-phenoxy-phenyl)-propenyl]-5-oxo-pyrrolidin-1-yl}-heptanoic acid (6) MS: 438 [(M+H)$^+$];

[2-(3-Ethoxy-phenyl)-2-oxo-ethyl]-phosphonic acid dimethyl ester gives 7-{(R)-2-[(E)-3-(3-ethoxy-phenyl)-3-hydroxy-propenyl]-5-oxo-pyrrolidin-1-yl}-heptanoic acid (7) MS: 390 [(M+H)$^+$];

[2-(3-Ethyl-phenyl)-2-oxo-ethyl]-phosphonic acid dimethyl ester gives 7-{(R)-2-[(E)-3-(3-ethyl-phenyl)-3-hydroxy-propenyl]-5-oxo-pyrrolidin-1-yl}-heptanoic acid (8) MS: 374 [(M+H)$^+$];

[2-(3-Morpholine-4-sulfonyl)-phenyl-2-oxo-ethyl] phosphonic acid dimethyl ester gives 7-((R)-2-{(E)-3-Hydroxy-3-[3-(morpholine-4-sulfonyl)-phenyl]-propenyl}-5-oxo-pyrrolidin-1-yl)-heptano acid (9) MS: 495 [(M+H)$^+$];

[2-(3-Bromo-phenyl)-2-oxo-ethyl]phosphonic acid dimethyl ester gives 7-{(R)-2-[(E)-3-(3-Bromo-phenyl)-3-hydroxy-propenyl]-5-oxo-pyrrolidin-1-yl}-heptanoic acid (10) MS: 425 [(M+H)$^+$];

[2-(3-Hydroxy-phenyl)-2-oxo-ethyl]phosphonic acid dimethyl ester gives 7-(R)-{2-[(E)-3-Hydroxy-3-(3-hydroxy-phenyl)-propenyl]-5-oxo-pyrrolidin-1-yl}-heptanoic acid (11) MS: 362 [(M+H)$^+$];

[2-(3-Pyrrol-1-ylmethyl-phenyl)-2-oxo-ethyl]phosphonic acid dimethyl ester gives 7-{(R)-2-[(E)-3-Hydroxy-3-(3-pyrrol-1-ylmethyl-phenyl)-propenyl]-5-oxo-pyrrolidin-1-yl}-heptanoic acid (12) MS: 425 [(M+H)$^+$];

[2-3-Pyrazol-1-ylmethyl-phenyl)-2-oxo-ethyl]phosphonic acid dimethyl ester gives 7-{(R)-2-[(E)-3-Hydroxy-3-(3-pyrazol-1-ylmethyl-phenyl)-propenyl]-5-oxo-pyrrolidin-1-yl}-heptanoic acid (13) MS: 426 [(M+H)$^+$];

[2-(3-methoxymethyl-phenyl)-2-oxo-ethyl]phosphonic acid dimethyl ester 7-{(R)-2-[(E)-3-Hydroxy-3-(3-methoxymethyl-phenyl)-propenyl]-5-oxo-pyrrolidin-1-yl}-heptanoic acid (14) MS: 390 [(M+H)$^+$].

[2-(3-cyclopentyloxy-phenyl)-2-oxo-ethyl]phosphonic acid dimethyl ester gives 7-{(R)-2-[(E)-3-(3-Cyclopentyloxy-phenyl)-3-hydroxy-propenyl]-5-oxo-pyrrolidin-1-yl}-heptanoic acid (15), MS: m/z 430 (M$^{+1}$);

[2-(3-trifluormethyl-phenyl)-2-oxo-ethyl]phosphonic acid dimethyl ester gives 7-{(R)-2-[(E)-3-Hydroxy-3-(3-trifluoromethyl-phenyl)-propenyl]-5-oxo-pyrrolidin-1-yl}-heptanoic acid (16), MS: m/z 414 (M$^{+1}$);

[2-(3-trifluormethyl-phenyl)-2-oxo-ethyl]phosphonic acid dimethyl ester gives 7-{(S)-2-[(R)-3-Hydroxy-3-(3-trifluoromethyl-phenyl)-propyl]-5-oxo-pyrrolidin-1-yl}-heptanoic acid [(17), following hydrogenation of the product of step 3 (1 atm hydrogen gas, catalytic 10% palladium on carbon in EtOAc, 1.5 h then subjected to reduction conditions described by E. J. Corey, et al., *J. Am. Chem. Soc.* 1987, 109, 7925–7926 using the (S)-2-methyl-CBS catalyst, 1 M toluene solution from Aldrich) instead of conducting the sodium borohydride treatment], MS: m/z 416 (M$^{+1}$);

[2-(3-phenoxymethyl-phenyl)-2-oxo-ethyl]phosphonic acid dimethyl ester gives 7-{(R)-2-[(E)-3-Hydroxy-3-(3- phenoxymethyl-phenyl)-propenyl]-5-oxo-pyrrolidin-1-yl}-heptanoic acid (18), MS: m/z 452 (M$^{+1}$);

7-{(R)-2-[(E)-3-Hydroxy-3-(3-phenoxymethyl-phenyl)-propenyl]-5-oxo-pyrrolidin-1-yl}-heptanoic acid methyl ester (19), MS: m/z 466 (M$^{+1}$);

2-[3-(1-methyl-1H-pyrrol-2-yl)-phenyl]2-oxo-ethyl] phosphonic acid dimethyl ester gives 7-((R)-2-{(E)-3-Hydroxy-3-[3-(1-methyl-1H-pyrrol-2-yl)-phenyl]-propenyl}-5-oxo-pyrrolidine-1-yl)-heptanoic acid (20), MS: m/z 425 (M$^{+1}$);

7-((R)-2-{(E)-3-Hydroxy-3-[3-(1-methyl-1H-pyrrol-2-yl)-phenyl]-propenyl}-5-oxo-pyrrolidin-1-yl)-heptanoic acid methyl ester (21), MS: n/z 440 (M$^{+1}$);

[2-(3-butoxy-phenyl)-2-oxo-ethyl]phosphonic acid dimethyl ester gives 7-{(R)-2-[(E)-3-(3-Butoxy-phenyl)-3-hydroxy-propenyl]-5-oxo-pyrrolidin-1-yl}-heptanoic acid (22), MS: m/z 418 (M$^{+1}$);

[2-(3-benzyloxy-phenyl)-2-oxo-ethyl]phosphonic acid dimethyl ester gives 7-{(R)-2-[(E)-3-(3-Benzyloxy-phenyl)-3-hydroxy-propenyl]-5-oxo-pyrrolidin-1-yl}-heptanoic acid (23), MS: m/z 452 (M$^{+1}$);

{2-[3-(2-chlorobenzyloxy)-phenyl]-2-oxo-ethyl}phosphonic acid dimethyl ester gives 7-{(R)-2-[(E)-3-(2-chlorobenzyloxy)-phenyl)-3-hydroxy-propenyl]-5-oxo-pyrrolidin-1-yl}-heptanoic acid (24), MS: m/z 487 (M$^{+1}$);

2-[2-biphenyl)-2-oxo-ethyl]phosphonic acid dimethyl ester gives 7-[(R)-2-((E)-3-Biphenyl-2-yl-3-hydroxy-propenyl)-5-oxo-pyrrolidin-1-yl]-heptanoic acid (25), MS: m/z 422 (M$^{+1}$);

[2-(3-(2-morpholino-4-yl-ethoxy)-phenyl)-2-oxo-ethyl] phosphonic acid dimethyl ester gives 7-((R)-2-{(E)-3-Hydroxy-3-[3-(2-morpholin-4-yl-ethoxy)-phenyl]-propenyl}-5-oxo-pyrrolidin-1-yl)-heptanoic acid (26), MS: m/z 475 (M$^{+1}$);

[3-(methyl-phenyl-amino)-phenyl-2-oxo-ethyl]phosphonic acid dimethyl ester gives 7-((R)-2-{(E)-3-Hydroxy-3-[3-(methyl-phenyl-amino)-phenyl]-propenyl}-5-oxo-pyrrolidin-1-yl)-heptanoic acid (27), MS: m/z 451 (M$^{+1}$);

[3-(methyl-o-tolyl-amino)-phenyl-2-oxo-ethyl]phosphonic acid dimethyl ester gives 7-((R)-2-{(E)-3-Hydroxy-3-[3-(methyl-o-tolyl-amino)-phenyl]-propenyl}-5-oxo-pyrrolidin-1-yl)-heptanoic acid (28), MS: m/z 465 (M$^{+1}$);

[2-(3-phenethyloxy-phenyl)-2-oxo-ethyl]phosphonic acid dimethyl ester gives 7-{(R)-2-[(E)-3-Hydroxy-3-(3-phenethyloxy-phenyl)-propenyl]-5-oxo-pyrrolidin-1-yl}-heptanoic acid (29), MS: m/z 466 (M$^{+1}$);

[2-{3-[2-(2-oxo-pyrrolidin-1-yl)-ethoxy]-phenyl}2-oxo-ethyl]phosphonic acid dimethyl ester gives 7-[(R)-2-((E)-3-Hydroxy-3-{3-[2-(2-oxo-pyrrolidin-1-yl)-ethoxy]-phenyl}-propenyl)-5-oxo-pyrrolidin-1-yl]-heptanoic acid (30), MS: m/z 473 (M$^{+1}$);

[2-[3-(2-tert-Butoxy-ethoxy)-phenyl]-2-oxo-ethyl] phosphonic acid dimethyl ester gives 7-((R)-2-{(E)-3-[3-(2-tert-butoxy-ethoxy)-phenyl]-3-hydroxy-propenyl}-5-oxo-pyrrolidin-1-yl)-heptanoic acid (31), MS: m/z 462 (M$^{+1}$);

[2-[3-indol-1-yl-phenyl]-2-oxo-ethyl]phosphonic acid dimethyl ester gives 7-{(R)-2-[(E)-3-Hydroxy-3-(3-indol-1-yl-phenyl)-propenyl]-5-oxo-pyrrolidin-1-yl}-heptanoic acid (32), MS: m/z 461 (M$^{+1}$);

{2-[(Z)-3-propenyl-phenyl]-2-oxo-ethyl}phosphonic acid dimethyl ester gives 7-{(R)-2-[(E)-3-Hydroxy-3-((Z)-3-propenyl-phenyl)-propenyl]-5-oxo-pyrrolidin-1-yl}-heptanoic acid (33), MS: m/z 386 (M$^{+1}$);

[2-(3-propyl-phenyl)-2-oxo-ethyl]phosphonic acid dimethyl ester gives 7-{(R)-2-[(E)-3-Hydroxy-3-(3-propyl-phenyl)-propenyl]-5-oxo-pyrrolidin-1-yl}-heptanoic acid (34), MS: m/z 388 (M$^{+1}$);

[2-(3-Dimethylcarbamoyl-phenyl)-2-oxo-ethyl]phosphonic acid dimethyl ester gives 7-{(R)-2-[(E)-3-(3-Dimethylcarbamoyl-phenyl)-3-hydroxy-propenyl]-5-oxo-pyrrolidin-1-yl}-heptanoic acid (35), MS: m/z 417 (M$^{+1}$);

{2-[3-(tetrahydro-pyran-4-ylidenemethyl)-phenyl]-2-oxo-ethyl}phosphonic acid dimethyl ester gives 7-((R)-2-{(E)-3-Hydroxy-3-[3-(tetrahydro-pyran-4-ylidenemethyl)-phenyl]-propenyl}-5-oxo-pyrrolidin-1-yl)-heptanoic acid (36), MS: m/z 442 (M$^{+1}$);

{2-[3-(tetrahydro-pyran-4-ylmethyl)-phenyl]-2-oxo-ethyl}phosphonic acid dimethyl ester gives 7-((R)-2-{(E)-3-Hydroxy-3-[3-(tetrahydro-pyran-4-ylmethyl)-phenyl]-propenyl}-5-oxo-pyrrolidin-1-yl)-heptanoic acid (37), MS: m/z 444 (M$^{+1}$);

{2-[3-(4-methoxy-benzyl)-phenyl]-2-oxo-ethyl}phosphonic acid dimethyl ester gives 7-((R)-2-{(E)-3-Hydroxy-3-[3-(4-methoxy-benzyl)-phenyl]-propenyl}-5-oxo-pyrrolidin-1-yl)-heptanoic acid (38), MS: m/z 466 (M$^{+1}$); and

[2-oxo-2-(5-trifluoromethyl-furan-2-yl)-ethyl]-phosphonic acid dimethyl ester gives 7-{(R)-2-[(E)-3-Hydroxy-3-(5-trifluoromethyl-furan-2-yl)-propenyl]-5-oxo-pyrrolidin-1-yl}-heptanoic acid (39), MS: m/z 404 (M$^{+1}$).

Example 2

7-{(R)-2-[(E)-3-(3-Benzoyl-phenyl)-3-hydroxy-propenyl]-5-oxo-pyrrolidin-1-yl-heptanoic Acid

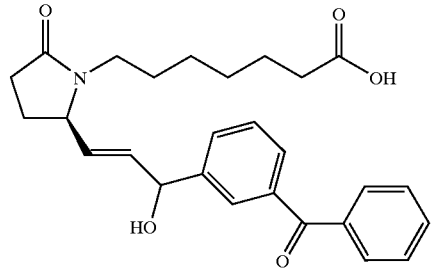

Step 1

3-(Dimethoxy-phenyl-methyl)-benzoic Acid Methyl Ester

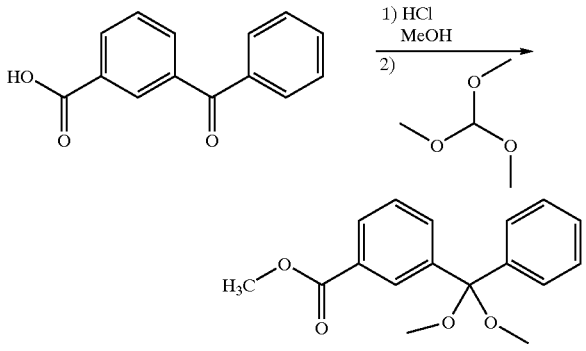

A methanol solution (15 mL) of 3-benzoyl-benzoic acid (2 g, 8.84 mmol) and methanesulfonic acid (0.115 mL, 1.77 mmol) was heated at 65° C. for 20 h and then cooled to room temperature. To this solution was added trimethyl orthoformate (1.45 mL, 13.26 mmol) and stirring continued for 24 h. The reaction solution was then diluted with ethyl acetate and washed with NaHCO$_3$. The organic layer was dried over MgSO$_4$, filtered and concentrated. Flash chromatography (20 hexanes: 1 ethyl acetate +0.25% triethyl amine) provided 3-(dimethoxy-phenyl-methyl)-benzoic acid methyl ester (951 mg) as an oil.

Step 2

{2-[3-(Dimethoxy-phenyl-methyl)-phenyl]-2-oxo-ethyl}-phosphonic Acid Dimethyl Ester

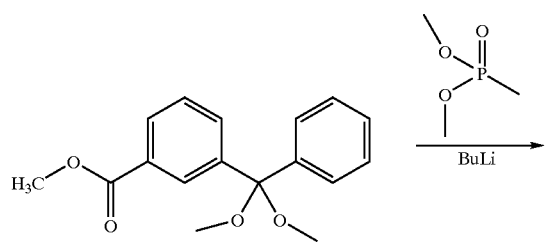

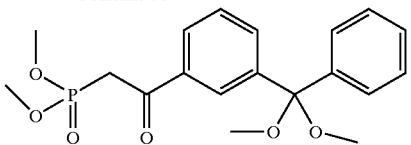

To a −78° C. THF solution (5 mL) of dimethylmethyl phosphonate (0.54 mL, 4.98 mmol) was added 1.6M BuLi (3.11 mL, 4.98 mmol). After stirring 40 min. a THF solution (5 mL) of 3-(dimethoxy-phenyl-methyl)-benzoic acid methyl ester (951 mg, 3.32 mmol) was added. After 15 min. the reaction mixture was warmed to room temperature. The reaction mixture was stirred an additional 1 h at room temperature and then quenched by the addition of NaHCO$_3$ solution. Dilution with ethyl acetate was followed by washing with NaHCO$_3$. The organic layer was dried over MgSO$_4$, filtered and concentrated. Flash chromatography (15 ethyl acetate: 1 hexanes+0.25% triethyl amine) provided {2-[3-(dimethoxy-phenyl-methyl)-phenyl]-2-oxo-ethyl}-phosphonic acid dimethyl ester (784 mg, 2.07 mmol) as an oil.

Step 3

7-((R)-2-{(E)-3-[3-(Dimethoxy-phenyl-methyl)-phenyl]-3-oxo-propenyl}-5-oxo-pyrrolidin-1-yl)-heptanoic Acid Ethyl Ester

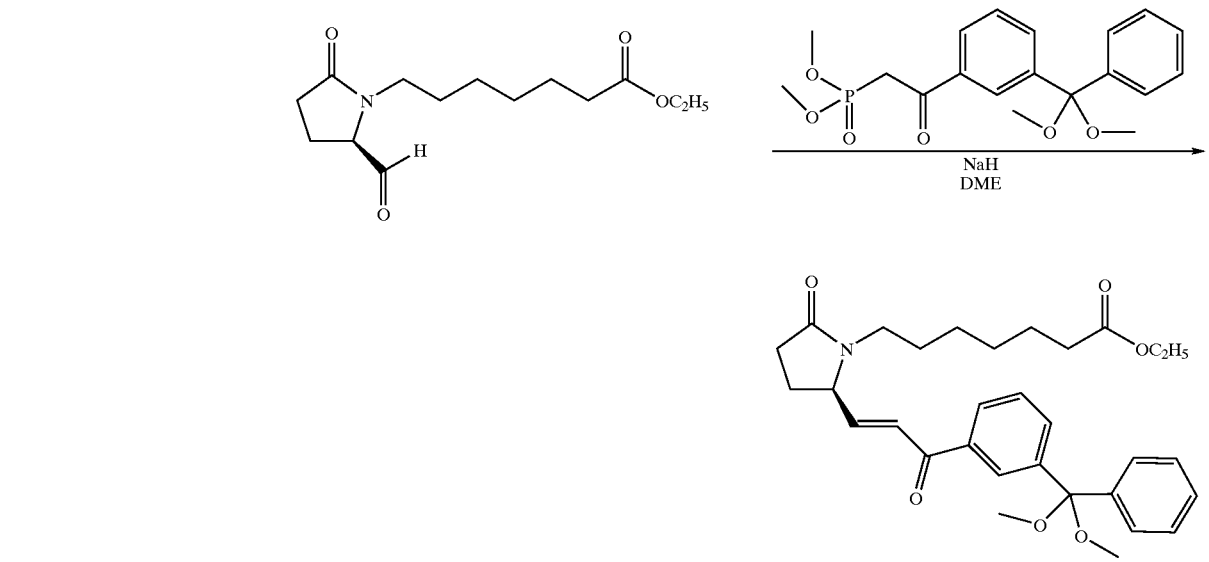

To 60% sodium hydride (20 mg, 0.51 mmol) was added a dimethoxyethane solution (5 mL) of {2-[3-(dimethoxy-phenyl-methyl)-phenyl]-2-oxo-ethyl}-phosphonic acid dimethyl ester (193 mg, 0.51 mmol). After 1.5 h a dimethoxyethane solution (5 mL) of 7-((R)-2-fFormyl-5-oxo-pyrrolidin-1-yl)-heptanoic acid ethyl ester (126 mg, 0.47 mmol) was added. The reaction mixture was stirred for 1 h, diluted with ethyl acetate and washed with NaHCO$_3$. The organic layer was dried over MgSO$_4$, filtered and concentrated. Flash chromatography (3 ethyl acetate: 1 hexanes+ 0.25% TEA) provided 7-((R)-2-{(E)-3-[3-(dimethoxy-phenyl-methyl)-phenyl]-3-oxo-propenyl}-5-oxo-pyrrolidin-1-yl)-heptanoic acid ethyl ester (124 mg, 0.24 mmol) as an oil.

Step 4

7-((R)-2-{(E)-3-[3-(Dimethoxy-phenyl-methyl)-phenyl]-3-hydroxy-propenyl}-5-oxo-pyrrolidin-1-yl)-heptanoic Acid

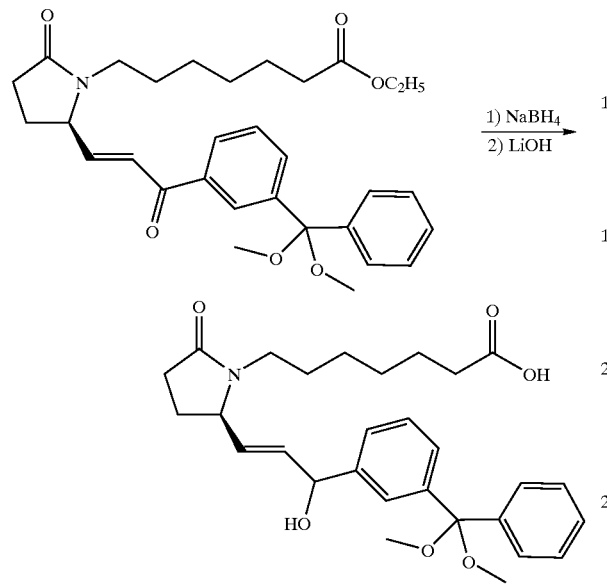

To an ethanol solution (5 mL) of 7-((R)-2-{(E)-3-[3-(dimethoxy-phenyl-methyl)-phenyl]-3-oxo-propenyl}-5-oxo-pyrrolidin-1-yl)-heptanoic acid ethyl ester (124 mg, 0.24 mmol) was added NaBH$_4$ (36 mg, 0.96 mmol). The reaction mixture was stirred for 2.25 h and then concentrated to dryness. The residue was dissolved in ethyl acetate and washed with NaHCO$_3$. The organic layer was dried over MgSO$_4$, filtered and concentrated to provide 7-((R)-2-{(E)-3-[3-(dimethoxy-phenyl-methyl)-phenyl]-3-hydroxy-propenyl}-5-oxo-pyrrolidin-1-yl)-heptanoic acid ethyl ester. To a methanol solution (5 mL) of 7-((R)-2-{(E)-3-[3-(dimethoxy-phenyl-methyl-phenyl]-3-hydroxy-propenyl}-5-oxo-pyrrolidin-1-yl)-heptanoic acid ethyl ester was added an aqueous solution (2.5 mL) of LiOH monohydrate (46 mg, 1.09 mmol). The reaction mixture was stirred for 6 h and then concentrated to remove the methanol. The aqueous concentrate was diluted with CH$_2$Cl$_2$ and 1 N HCl was added, extracted with CH$_2$Cl$_2$ and dried over MgSO$_4$. This mixture was filtered and concentrated to yield 7-((R)-2-{(E)-3-[3-(dimethoxy-phenyl-methyl)-phenyl]-3-hydroxy-propenyl}-5-oxo-pyrrolidin-1-yl)-heptanoic acid (116 mg, 0.23 mmol) as an oil.

Step 5

7-{(R)-2-[(E)-3-(3-Benzoyl-phenyl)-3-hydroxy-propenyl]-5-oxo-pyrrolidin-1-yl}-heptanoic Acid

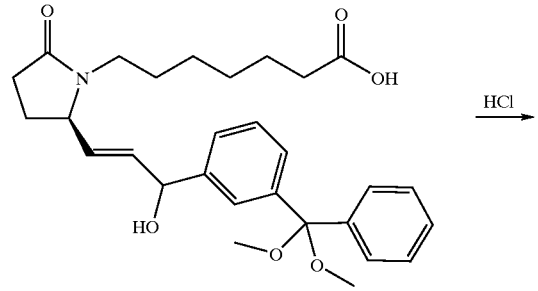

HCl →

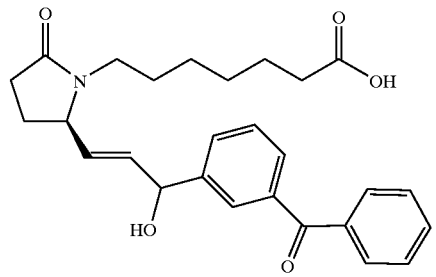

A p-dioxane solution (5 mL) of acid/ketal 7-((R)-2-{(E)-3-[3-(dimethoxy-phenyl-methyl)-phenyl]-3-hydroxy-propenyl}-5-oxo-pyrrolidin-1-yl)-heptanoic acid (116 mg, 0.23 mmol) was stirred with 1N HCL (1 mL, 1.0 mmol) for 18 h. The reaction solution was diluted with ethyl acetate and washed with NaHCO$_3$. The organic layer was dried over MgSO$_4$, filtered and concentrated to provide 7-{(R)-2-[(E)-3-(3-benzoyl-phenyl)-3-hydroxy-propenyl]-5-oxo-pyrrolidin-1-yl}-heptanoic acid (40)(83 mg, 0.18 mmol) as an oil; MS: 450 [(M+H)$^+$].

Similarly replacing {2-[3-(dimethoxy-phenyl-methyl)-phenyl]-2-oxo-ethyl}-phosphonic acid dimethyl ester in Step 3 with the following appropriate phosphonates prepared from the corresponding known acids or esters as described in steps 1 and/or 2, the following compound of Formula I was prepared:

(2-{3-[dimethoxy-(4-methoxyphenyl)-methyl]-phenyl}-2-oxo-ethyl)-phosphonic acid dimethyl ester 7-[(R)-2-((E)-3-Hydroxy-3-{3-[1-(4-methoxy-phenyl)-methanoyl]-phenyl}-propenyl)-5-oxo-pyrrolidin-1-yl]-heptanoic acid (41), MS: m/z 480 (M$^{+1}$).

Example 3

7-{(R)-2-[(E)-3-Hydroxy-3-(2'-methyl-biphenyl-3-yl)-propenyl]-5-oxo-pyrrolidin-1-yl}-heptanoic Acid Methyl Ester(42)

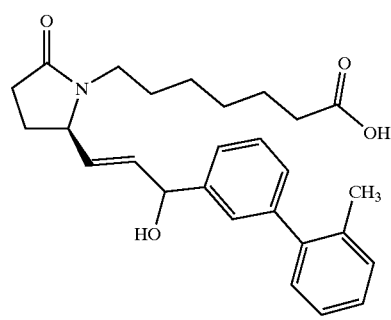

Step 1

7-{(R)-2-[(E)-3-(3-Bromo-phenyl)-3-oxo-propenyl]-5-oxo-pyrrolidin-1-yl}-heptanoic Acid Methyl Ester

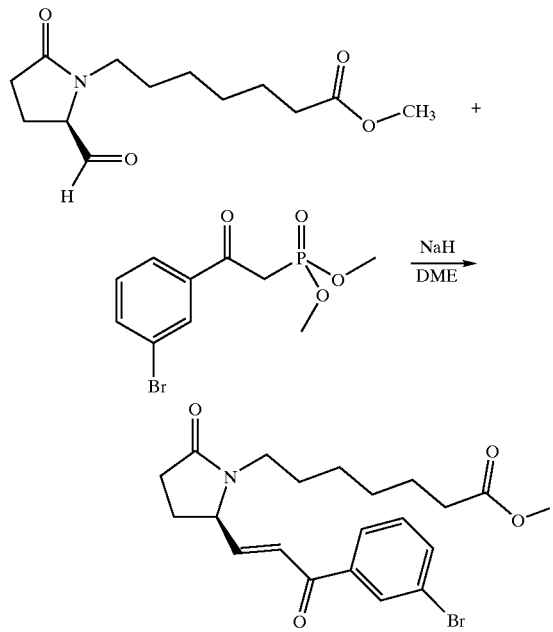

To a solution of NaH (0.14 g, 1 eq) in 30 mL of ethylene glycol dimethyl ether stirred at 0° C. under nitrogen was added [2-(3-bromo-phenyl)-2-oxo-ethyl]-phosphonic acid dimethyl ester (1.82 g, 1.05 eq). After 1 hour at 0° C., 7-((R)-2-formyl-5-oxo-pyrrolidin-1-yl)-heptanoic acid methyl ester (1.44 g, 5.64 mmol) in 2 mL of DME was added slowly. The ice bath was removed and then the mixture was stirred for an additional 3 hours at room temperature. Saturated ammonium chloride solution was added and the solution was extracted with ethyl acetate. The organic layer was dried over anhydrous magnesium sulfate, concentrated under reduced pressure, and purified by chromatography. EtOAc(1):Hexane(1)followed by EtOAc(5):Hexane(1) to yield 1.6 g of 7-{(R)-2-[(E)-3-(3-bromo-phenyl)-3-oxo-propenyl]-5-oxo-pyrrolidin-1-yl}-heptanoic acid methyl ester.

Step 2

7-{(R)-2-[(E)-3-(3-Bromo-phenyl)-3-hydroxy-propenyl]-5-oxo-pyrrolidin-1-yl}-heptanoic Acid Methyl Ester

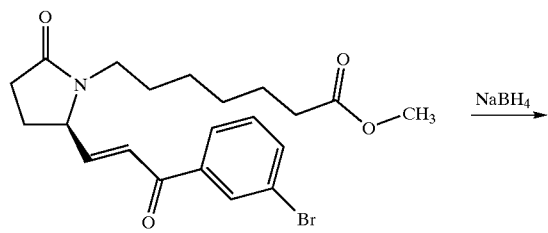

-continued

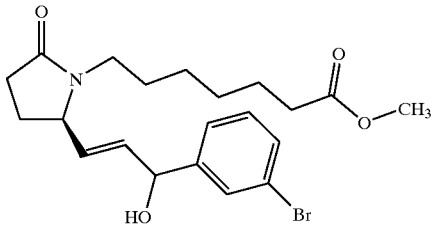

To a solution of 7-{(R)-2-[(E)-3-(3-bromo-phenyl)-3-oxo-propenyl]-5-oxo-pyrrolidin-1-yl}-heptanoic acid methyl ester (0.78 g, 1.79 mmol) in 15 mL of methanol stirred at 0° C. under nitrogen was added sodium borohydride (0.074 g). The reaction mixture was stirred at room temperature for 6 hours. After addition of 1 N HCl solution the mixture was extracted with ethyl acetate. The organic layer was dried over anhydrous magnesium sulfate, concentrated, and purified by chromatography eluting with 50% EtOAc and Hexane followed by 100% EtOAc to yield 670 mg of 7-{(R)-2-[(E)-3-(3-bromo-phenyl)-3-hydroxy-propenyl]-5-oxo-pyrrolidin-1-yl}-heptanoic acid methyl ester.

Step 3

7-{(R)-2-[(E)-3-Hydroxy-3-(2'-methyl-biphenyl-3-yl)-propenyl]-5-oxo-pyrrolidin-1-yl}-hepatonic Acid Methyl Ester

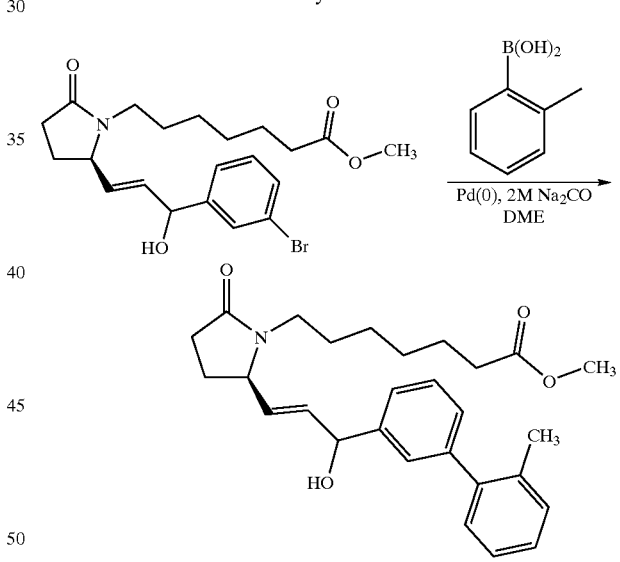

To a solution of 7-{(R)-2-[(E)-3-(3-bromo-phenyl)-3-hydroxy-propenyl]-5-oxo-pyrrolidin-1-yl}-heptanoic acid methyl ester, (0.2 g, 0.46 mmol) in 10 mL of DME stirred at room temperature was added Pd(Ph₃P)₄ (0.03 g, 0.05 eq). After stirring for 5 minutes, o-tolylboronic acid (0.12 g, 2 eq) an 2M Na₂CO₃ (0.6 mL, 2.5eq) were added and the mixture was refluxed overnight under N₂ atmosphere. The reaction mixture was cooled to room temperature, diluted with 25% NH₄Oac (10 mL), stirred for 5 minutes and then was extracted with ethyl acetate, the organic layer was dried over MgSO₄ (anhydrous), concentrated under the reduced pressure and purified to yield 87 mg of 7-{(R)-2-[(E)-3-hydroxy-3-(2'-methyl-biphenyl-3-yl)-propenyl]-5-oxo-pyrrolidin-1-yl}-heptanoic acid methyl ester.

Step 4

7-{(R)-2-[(E)-3-Hydroxy-3-(2'-methyl-biphenyl-3-yl)-propenyl]-5-oxo-pyrrolidin-1-yl}-heptanoic Acid

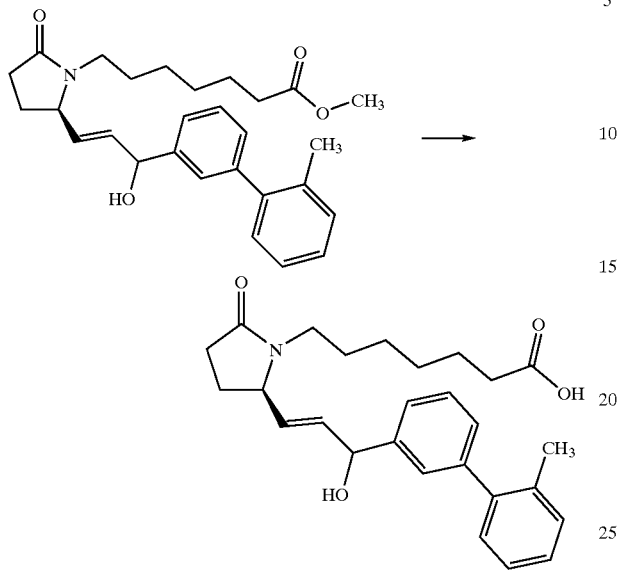

To a methanol solution (5 mL) of 7-{(R)-2-[(E)-3-Hydroxy-3-(2'-methyl-biphenyl-3-yl)-propenyl]-5-oxo-pyrrolidin-1-yl}-heptanoic acid methyl ester (87 mg) was added an aqueous solution (2.5 mL) of LiOH monohydrate. The reaction mixture was stirred for 6 h and then concentrated to remove the methanol. The aqueous concentrate was diluted with $CH_2Cl_2$ and 1N HCl was added, extracted with $CH_2Cl_2$ and dried over $MgSO_4$. This mixture was filtered and concentrated to yield 62 mg of 7-{(R)-2-[(E)-3-Hydroxy-3-(2'-methyl-biphenyl-3-yl)-propenyl]-5-oxo-pyrrolidin-1-yl}-heptanoic acid as an oil (42) (50).MS:435 [(M+H)$^+$].

Similarly replacing o-tolylboronic acid in Step 3 with appropriately substituted phenylboronic acid the following compounds were prepared:

7-[(R)-2-((E)-3-Biphenyl-3-yl-3-hydroxy-propenyl)-5-oxo-pyrrolidin-1-yl]-heptanoic acid (43), MS: m/z 422 [(M$^{+1}$)$^+$];

7-{(R)-2-[(E)-3-(2'-Ethoxy-biphenyl-3-yl)-3-hydroxy-propenyl]-5-oxo-pyrrolidin-1-yl}-heptanoic acid (44), MS: m/z 466 [(M$^{+1}$)$^+$];

7-{(R)-2-[(E)-3-(2'-Chloro-biphenyl-3-yl)-3-hydroxy-propenyl]-5-oxo-pyrrolidin-1-yl}-heptanoic acid (45), MS: m/z 457 [(M$^{+1}$)$^+$];

7-{(R)-2-[(E)-3-(4'-Chloro-biphenyl-3-yl)-3-hydroxy-propenyl]-5-oxo-pyrrolidin-1-yl}-heptanoic acid (46), MS: m/z 457 [(M$^{+1}$)$^+$];

7-{(R)-2-[(E)-3-(3'-Chloro-biphenyl-3-yl)-3-hydroxy-propenyl]-5-oxo-pyrrolidin-1-yl}-heptanoic acid (47), MS: m/z 457 [(M$^{+1}$)$^+$];

7-{(R)-2-[(E)-3-(4'-Chloro-2'-methyl-biphenyl-3-yl)-3-hydroxy-propenyl]-5-oxo-pyrrolidin-1-yl}-heptanoic acid (48), MS: m/z 471 [(M$^{+1}$)$^+$];

7-{(R)-2-[(E)-3-(4'-Hydroxy-2'-methyl-biphenyl-3-yl)-3-hydroxy-propenyl]-5-oxo-pyrrolidin-1-yl}-heptanoic acid (49), MS: m/z 452 [(M$^{+1}$)$^+$];

7-{(R)-2-[(E)-3-(4'-Chloro-2'-methyl-biphenyl-3-yl)-3-hydroxy-propyl]-5-oxo-pyrrolidin-1-yl}-heptanoic acid [(50), was prepared following hydrogenation of the product of step 1, 1 atm hydrogen gas with 10% palladium on carbon in EtOAc, 1.5 h), MS: m/z 473 [(M$^{+1}$)$^+$];

7-{(S)-2-[(R)-3-Hydroxy-3-(4'-hydroxy-2'-methyl-biphenyl-3-yl)-propyl]-5-oxo-pyrrolidin-1-yl}-heptanoic acid [(51), was produced after step 3 while excluding the treatment described in step 2; 1 atm hydrogen gas, catalytic 10% palladium on carbon in EtOAc, 1.5 h and then subjected to reduction conditions described by E. J. Corey, et al., J. Am. Chem. Soc. 1987, 109, 7925–7926 using the (S)-2-methyl-CBS catalyst, 1 M toluene solution from Aldrich], MS: m/z 454 [(M$^{+1}$)$^+$].

Similarly use of [2-(3-Bromo-4-methyl-phenyl)-2-oxo-ethyl]phosphonic acid dimethyl ester in step 1 gives 7-{(R)-2-[(E)-3-(6,2'-Dimethyl-biphenyl-3-yl)-3-hydroxy-propenyl]-5-oxo-pyrrolidin-1-yl}-heptanoic acid (52), MS: 362 [(M+H)$^+$].

Example 4

7-{(S)-2-[3-(1-Benzyl-1H-pyrazol-4-yl)-3-hydroxy-propyl]-5-oxo-pyrrolidin-1-yl}-heptanoic Acid (53)

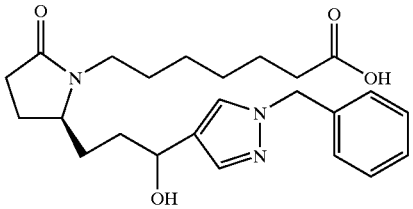

Step 1

[2-(1-Benzyl-1H-pyrazol-4-yl)-2-oxo-ethyl]-phosphonic Acid Dimethyl Ester

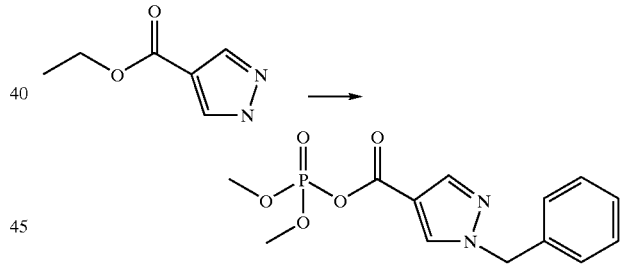

A suspension of ethyl 4-pyrazole carboxylate (2.2 g, 15.7 mmol) and cesium carbonate (5.2 g, 15.7 mmol) in dimethylformamide (100 mL) at ambient temperature was treated with benzyl bromide (1.9 mL, 15.7 mmol). The mixture was heated to 90° C. for 45 minutes, cooled to ambient temperature, and partitioned between water (400 mL) and 1:1 hexane:ethyl acetate (4×150 mL). The combined organic extracts were washed with brine (2×100 mL) and stored over anhydrous magnesium sulfate. The volatiles were removed and the residue was loaded onto a column of silica gel. The desired product eluted with 3:1 hexane:ethyl acetate and was obtained as a white solid (3.4 g). In a separate vessel, a tetrahydrofuran (80 mL) solution of dimethyl methylphosphonate (Aldrich, 1.6 mL, 15 mmol) was cooled to −78° C. and treated with normal-butyllithium (6.0 mL, 15 mmol). After 45 minutes, a tetrahydrofuran (20 mL) solution of the ester above (2.3 g, 10 mmol) was added and the mixture was warmed to 0° C. over 30 minutes. The mixture was poured into aqueous ammonium chloride and extracted with ethyl acetate (2×100 mL). The combined organic extracts was washed with fresh water (2×50 mL) then brine and stored over anhydrous sodium sulfate. The volatiles were removed by rotary evaporator and the residue loaded onto a column of silica gel. The desired [2-(1-benzyl-1H-pyrazol-4-yl)-2-oxo-ethyl]-phosphonic acid dimethyl ester was eluted with 20:1 ethyl acetate:methanol and was obtained as an oil (1.68 g).

Step 2

7-{(R)-2-[(E)-4-(1-Benzyl-1H-pyrazol-4-yl)-3-oxo-but-1-enyl]-5-oxo-pyrrolidin-1-yl}-heptanoic Acid Ethyl Ester

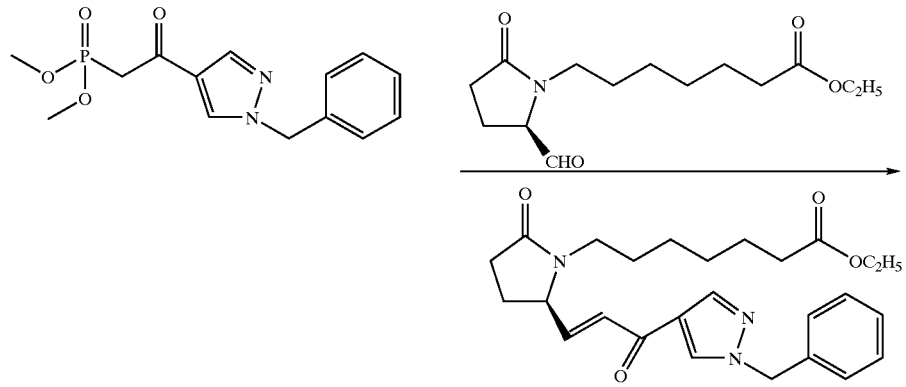

7-{(R)-2-[(E)-4-(1-Benzyl-1H-pyrazol-4-yl)-3-oxo-but-1-enyl]-5-oxo-pyrrolidin-1-yl}-heptanoic acid ethyl ester was produced according to Example 1 Step 3, using [2-(1-benzyl-1H-pyrazol-4-yl)-2-oxo-ethyl]-phosphonic acid dimethyl ester (820 mg, 2.66 mmol) in dimethoxyethane with sodium hydride (95%, 70 mg, 2.66 mmol) and 7-((R)-2-formyl-5-oxo-pyrrolidin-1-yl)-heptanoic acid ethyl ester (ca. 800 mg, 2.8 mmol). The desired enone (419 mg, 0.93 mmol) was isolated as an oil.

Step 3

7-{(R)-2-[(E)-4-(1-Benzyl-1H-pyrazol-4-yl)-3-oxo-but-1-enyl]-5-oxo-pyrrolidin-1-yl}-heptanoic Acid

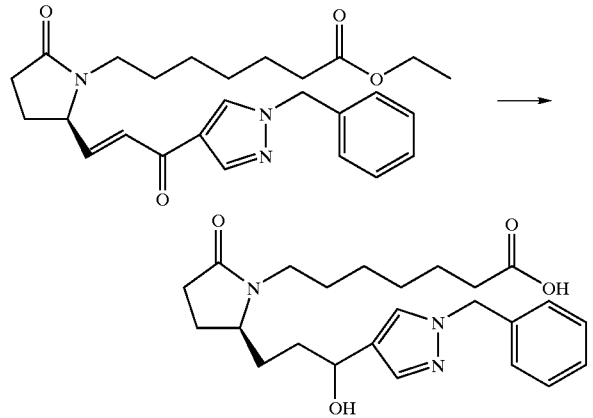

The pyrazole-containing enone (210 mg, 0.46 mmol) was dissolved in methanol (5 mL), cooled to 0° C. and treated with sodium borohydride (50 mg, 1.3 mmol). After stirring at ambient temperature for 15 minutes, acetone (2 mL) was added and the volatiles were removed. Methanol was added again and the volatiles were removed again. The residue was suspended in 0.05 M aqueous phosphate solution at pH 6.5 (ca. 50 mL) and treated with Lipase type VII (Sigma, 2 g) and stirred vigorously for 2 hours at ambient temperature. The suspension was diluted with diethyl ether (ca. 25 mL) and filtered through a pad of Celite. The layers were separated and the aqueous layer was washed again with ether. The aqueous layer was now acidified with glacial acetic acid and extracted with ethyl acetate (4×25 mL). The combined organic extracts were stored over anhydrous sodium sulfate. Following filtration, the desired 7-{(R)-2-[(E)-4-(1-benzyl-1H-pyrazol-4-yl)-3-oxo-but-1-enyl]-5-oxo-pyrrolidin-1-yl}-heptanoic acid (53) (70) (109 mg, 0.25 mmol) was obtained following removal of the volatiles: MS: 428 [(M+H)$^+$].

Example 5

7-{(S)-2-[3-Hydroxy-3-(5-o-tolyl-furan-2-yl)-propyl]-5-oxo-pyrrolidin-1-yl}-heptanoic Acid (54)

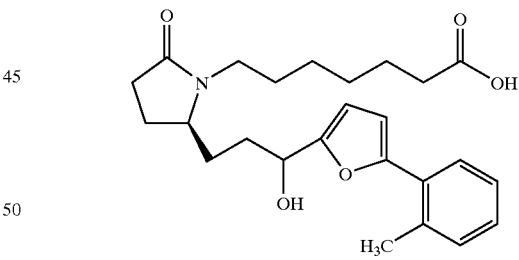

Step 1

[2-(5-Bromo-furan-2-yl)-2-oxo-ethyl]-phosphonic Acid Dimethyl Ester

The methyl ester of 5-bromo-2-furoic acid was prepared upon treatment with trimethylsilyldiazomethane. The ester (10.2 g, 47 mmol) was dissolved in tetrahydrofuran (40 mL) and added to a −78° C. solution of lithiated dimethyl methylphosphonate (90 mmol). The desired [2-(5-bromo-furan-2-yl)-2-oxo-ethyl]-phosphonic acid dimethyl ester (5.83 g, 19.5 mmol) was isolated as described above:.

Step 2

7-{(R)-2-[(E)-3-(5-Bromo-furan-2-yl)-3-oxo-propenyl]-5-oxo-pyrrolidin-1-yl}-heptanoic Acid Ethyl Ester

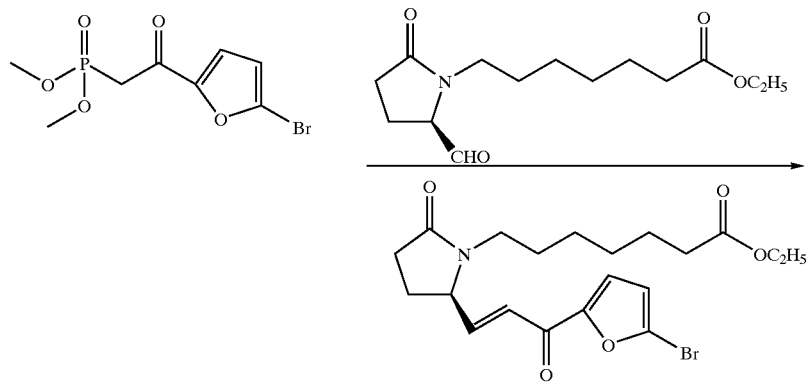

The 7-{(R)-2-[(E)-3-(5-Bromo-furan-2-yl)-3-oxo-propenyl]-5-oxo-pyrrolidin-1-yl}-heptanoic acid ethyl ester above was prepared as described in Example 4 Step 1 using the 5-bromo-2-furoyl phosphonate (1.12 g, 3.8 mmol) as a solution in dimethoxyethane (95 mL), sodium hydride (95%, 91 mg, 3.6 mmol) and then treated with 7-((R)-2-formyl-5-oxo-pyrrolidin-1-yl)-heptanoic acid methyl ester (1.2 g, 4 mmol): to yield 7-{(R)-2-[(E)-3-(5-bromo-furan-2-yl)-3-oxo-propenyl]-5-oxo-pyrrolidin-1-yl}-heptanoic acid ethyl ester MS: 442 (M+1 with $^{81}$Br), 440 (M+1 with $^{79}$Br).

Step 3

7-{(S)-2-[3-Hydroxy-3-(5-o-tolyl-furan-2-yl)-propyl]-5-oxo-pyrrolidin-1-yl}-heptanoic Acid

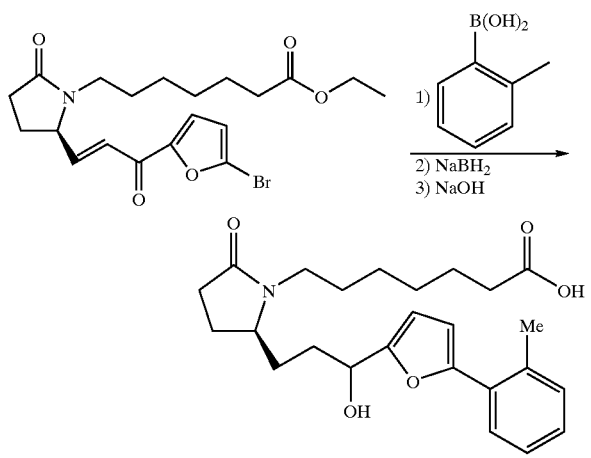

7-{(R)-2-[(E)-3-(5-Bromo-furan-2-yl)-3-oxo-propenyl]-5-oxo-pyrrolidin-1-yl}-heptanoic acid ethyl ester was dissolved in anhydrous 1,4-dioxane (3 mL) under an argon atmosphere treated with potassium carbonate (130 mg, 0.94 mmol), 2-methylphenyl boronic acid (64 mg, 0.47 mmol), and bis(triphenylphosphine)palladiumdichloride (33 mg, 0.047 mmol). The yellow suspension was warmed to 55° C. for 15 hours and then the volatiles were removed. The mixture was then dissolved in methanol (10 mL) and stirred with sodium borohydride (ca. 35 mg, 0.9 mmol) for 20 minutes at ambient temperature and treated with acetone (1 mL). After removal of the volatiles, the residue was treated with methanol and the volatiles were removed once again. The residue was loaded onto 1 mm thick silica plates and the plates were developed two-times with 3% iso-propanol in dichloromethane. 7-{(S)-2-[3-hydroxy-3-(5-o-tolyl-furan-2-yl)-propyl]-5-oxo-pyrrolidin-1-yl}-heptanoic acid ethyl ester (54 mg) was obtained as an oil.

The ester (54 mg) was dissolved in methanol (3 mL) and treated with 5 M aqueous solution of sodium hydroxide (0.5 mL) and stirred at ambient temperature for 1 hour. 7-{(S)-2-[3-hydroxy-3-(5-o-tolyl-furan-2-yl)-propyl]-5-oxo-pyrrolidin-1-yl}-heptanoic acid (54) (71) (45 mg, 0.10 mmol) resulted upon treatment with 1 M aqueous hydrochloric acid and extraction with ethyl acetate: MS: 428 [(M+H)$^+$].

Example 6

7-1 (R)-5-[(E)-3-Hydroxy-3-(5-trifluoromethyl-furan-2-yl)-propenyl]-3,3-dimethyl-2-oxo-pyrrolidin-1-yl}-heptanoic Acid (55)

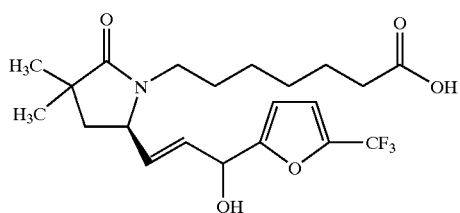

Step 1

(R)-5-(1-Ethoxy-ethoxymethyl)-3,3-dimethyl-pyrrolidin-2-one

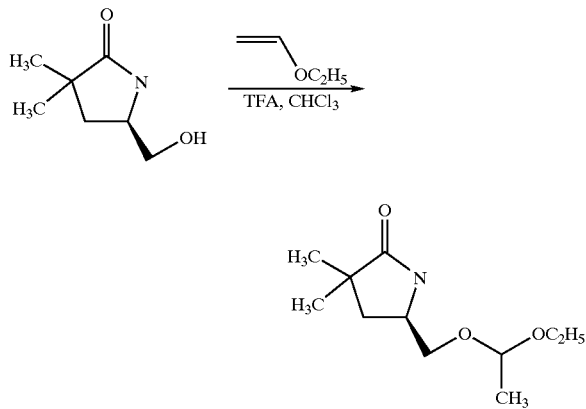

To a solution of (R)-5-hydroxymethyl-3,3-dimethyl-pyrrolidin-2-one (4.0 g, 28 mmol), prepared as described in *Tetrahedron* 1998, 54 10295–10307, and ethyl vinyl ether (4 mL, 42 mmol) in chloroform (26 mL), was added a catalytic amount of trifluoroacetic acid (0.056 mL), and the reaction mixture was stirred for four hours at room temperature. The solution was then washed with a saturated solution of sodium bicarbonate and brine, and dried over magnesium sulfate. The crude oil obtained after evaporating the solvent, was purified by chromatography on silica gel using hexane-:ethyl acetate 1:1 as a solvent, giving 2.6 g of (R)-5-(1-ethoxy-ethoxymethyl)-3,3-dimethyl-pyrrolidin-2-one.

Step 2

7-((R)-5-Hydroxymethyl-3,3-dimethyl-2-oxo-pyrrolidin-1-yl)-heptanoic Acid Ethyl Ester

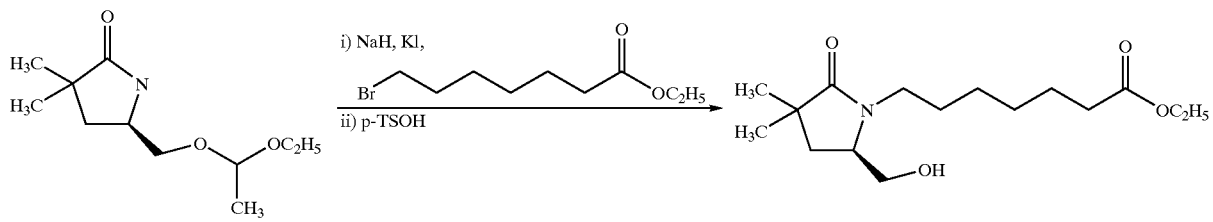

A solution of (R)-5-(1-ethoxy-ethoxymethyl)-3,3-dimethyl-pyrrolidin-2-one (2.58 g, 11.2 mmol) in dimethylformamide (4 mL) was slowly added to a suspension of sodium hydride 60% (450 mg, 11.2 mmol) and potassium iodide (2.27 g, 13.7 mmol) in dimethylformamide (13 mL) at 0° C. under nitrogen. After stirring for one hour at room temperature, a solution of ethyl-7-bromoheptanoate (2.66 mL, 13.7 mmol) in dimethylformamide (5 mL) was added to the reaction mixture, and the flask was warmed to 50° C. for 72 hours. The solvent was then removed under vacuum and the residue was taken up in ethyl acetate. The solution was washed with brine and dried over magnesium sulfate.

The residue obtained after concentration was dissolved in methanol (40 mL), and catalytic amounts of paratoluene-sulfonic acid monohydrate (170 mg) were added to the solution. The reaction mixture was stirred for seven hours until deprotection was completed. The solvent was then removed under vacuum and the residue dissolved in ethyl acetate. The solution was washed with saturated solution of sodium bicarbonate and brine, and dried over magnesium sulfate. The crude obtained after concentration under vacuum was purified by chromatography on silica gel, using hexane:ethyl acetate 2:1 to 1:2 as a solvent to afford 2.3 g of 7-((R)-5-hydroxymethyl-3,3-dimethyl-2-oxo-pyrrolidin-1-yl)-heptanoic acid ethyl ester as a transparent oil.

Step 3

7-((R)-5-Formyl-3,3-dimethyl-2-oxo-pyrrolidin-1-yl)-heptanoic Acid Ethyl Ester

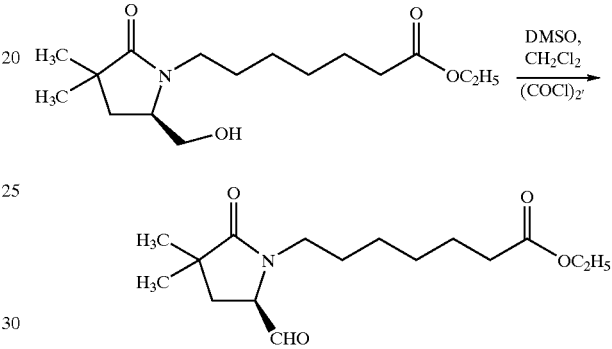

A solution of dimethylsulfoxide (0.93 mL, 12 mmol) in dichloromethane (40 mL) was cooled to −78° C. under nitrogen, and a solution of oxalyl chloride (0.820 mL, 9.4 mmol) in dichloromethane (3 mL) was added to it, over a 2 minute period. The reaction mixture was left stirring at −78° C. for 30 minutes. A solution of 7-((R)-5-hydroxymethyl-3,3-dimethyl-2-oxo-pyrrolidin-1-yl)-heptanoic acid ethyl ester (2.25 g, 7.5 mmol) in dichloromethane (20 mL) was added slowly. When the addition was complete, the reaction flask was stirred for 15 minutes at −78° C. Finally, triethylamine (2.1 mL, 15.0 mmol) was added slowly to the reaction flask; it was left to reach room temperature and stirred for an additional 15 minutes. It was then quenched by adding 20 mL of water and 20 mL of diethyl ether, and extracted with dichloromethane. The organic phase was dried over potassium carbonate and concentrated to dryness. The crude mixture was purified by chromatography on silica gel using hexane:ethyl acetate 2:1 as a solvent giving 1.5 g of 7-((R)-5-formyl-3,3-dimethyl-2-oxo-pyrrolidin-1-yl)-heptanoic acid ethyl ester.

Step 4

7-{(R)-3,3-Dimethyl-2-oxo-5-[(E)-3-oxo-3-(5-trifluoromethyl-furan-2-yl)-propenyl]-pyrrolidin-1-yl}-heptanoic Acid Ethyl Ester

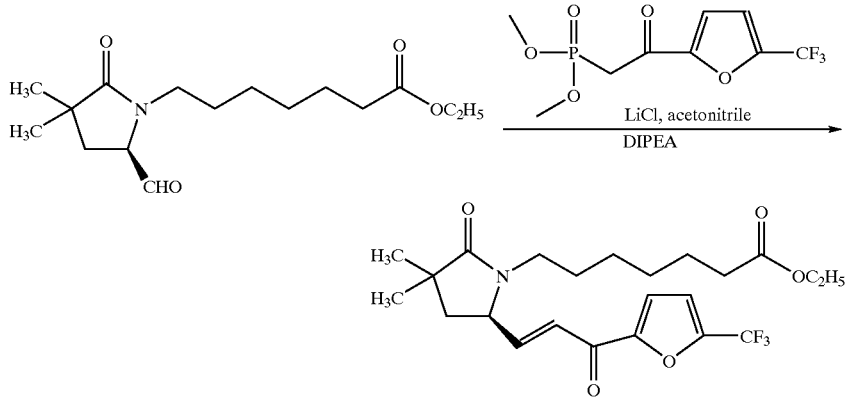

To a stirred solution of 7-((R)-5-formyl-3,3-dimethyl-2-oxo-pyrrolidin-1-yl)-heptanoic acid ethyl ester. (360 mg, 1.21 mmol) and [2-oxo-2-(5-trifluoromethyl-furan-2-yl)-ethyl]-phosphonic acid dimethyl ester (344 mg, 1.21 mmol) (prepared from 5-trifluoromethyl-furan-2-carboxylic acid as described herein) in acetonitrile (14 mL), were added lithium chloride (62 mg, 1.21 mmol) and diisopropylethyl amine (0.214 mL, 1.21 mmol). The reaction flask was left stirring at room temperature over the weekend. The reaction was then quenched with a saturated solution of ammonium chloride and extracted with ethyl acetate. The organic phase was then washed with brine and dried over magnesium sulfate, and the crude was purified on silicagel column using hexane:ethyl acetate 2:1. Evaporation of the solvent gave 280 mg of 7-{(R)-3,3-dimethyl-2-oxo-5-[(E)-3-oxo-3-(5-trifluoromethyl-furan-2-yl)-propenyl]-pyrrolidin-1-yl}-heptanoic acid ethyl ester.

Step 5

7-{(R)-5-[(E)-3-Hydroxy-3-(5-trifluoromethyl-furan-2-yl)-propenyl]-3,3-dimethyl-2-oxo-pyrrolidin-1-yl}-heptanoic Acid Ethyl Ester

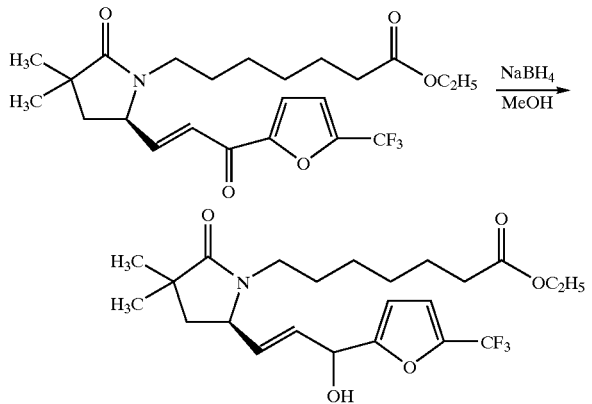

Sodium borohydride (37 mg, 0.98 mmol) was slowly added to a solution of 7-{(R)-3,3-dimethyl-2-oxo-5-[(E)-3-oxo-3-(5-trifluoromethyl-furan-2-yl)-propenyl]-pyrrolidin-1-yl}-heptanoic acid ethyl ester (280 mg, 0.61 mmol) in methanol (4 mL) at −20° C. The reaction flask was kept at −10° C. for 45 minutes. When the addition was complete the reaction vessel was kept at −10 C for 40 min. When the reaction was done, it was quenched with acetone and concentrated to dryness. The residue was dissolved in ethyl acetate, washed with brine and dried. After concentration, the crude mixture was purified on a silica gel column using hexane:ethyl acetate 1:1 as the solvent, giving 90 mg of 7-{(R)-5-[(E)-3-hydroxy-3-(5-trifluoromethyl-furan-2-yl)-propenyl]-3,3-dimethyl-2-oxo-pyrrolidin-1-yl}-heptanoic acid ethyl ester.

Step 6

7-{(R)-5-[(E)-3-Hydroxy-3-(5-trifluoromethyl-furan-2-yl)-propenyl]-3,3-dimethyl-2-oxo-pyrrolidin-1-yl}-heptanoic Acid

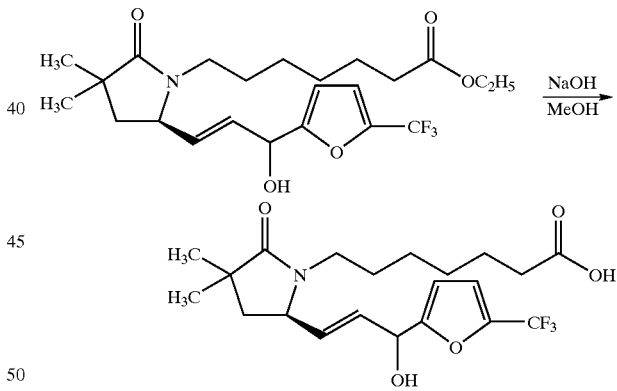

7-{(R)-5-[(E)-3-hydroxy-3-(5-trifluoromethyl-furan-2-yl)-propenyl]-3,3-dimethyl-2-oxo-pyrrolidin-1-yl}-heptanoic acid ethyl ester (89 mg, 0.2 mmol) was dissolved in methanol (3 mL) and the solution cooled in an ice bath. A 20% solution of sodium hydroxide (0.280 mL, 1.4 mmol) was slowly added and when the addition was complete, the reaction flask was left stirring overnight at room temperature. The reaction solution was concentrated under vacuum; the residue was suspended in 5 mL of 0.1 N solution of sodium hydroxide and it was washed twice with diethyl ether. The solution was then acidified with 1 N hydrochloric acid and extracted three times with ethyl acetate. The organic layer was washed with brine and dried over magnesium sulfate giving after concentration 55 mg of 7-{(R)-5-[(E)-3-hydroxy-3-(5-trifluoromethyl-furan-2-yl)- propenyl]-3,3-dimethyl-2-oxo-pyrrolidin-1-yl}-heptanoic acid (55) (80). MS: 432 [(M+H)⁺].

Similarly replacing the following appropriate intermediates, the following compounds of Formula I were prepared:

The use of dimethyl (2-oxoheptyl)phosphonate in step 4 gives 7-[(R)-5-((E)-3-hydroxy-oct-1-enyl)-3,3-dimethyl-2-oxo-pyrrolidin-1-yl]-heptanoic acid (56), MS: m/z 368 (M⁺¹);

4,4-dimethyl-5-hydroxymethyl-2-pyrrolidinone in step 1 gives 7-[2-((E)-3-hydroxy-oct-1-enyl)-3,3-dimethyl-5-oxo-pyrrolidin-1-yl]-heptanoic acid (57), MS: m/z 368 (M⁺¹);

[2-(cyclobutyl-ethyl)-2-oxo-ethyl]phosphonic acid dimethyl ester in step 4 gives 7-[(R)-5-((S)-(E)-5-Cyclobutyl-3-hydroxy-pent-1-enyl)-3,3-dimethyl-2-oxo-pyrrolidin-1-yl]-heptanoic acid (58), MS: m/z 380 (M⁺¹);

{2-[(3-methoxymethyl-phenyl)methyl]-2-oxo-ethyl}phosphonic acid dimethyl ester in step 4 gives 7-{(R)-5-[(E)-3-Hydroxy-4-(3-methoxymethyl-phenyl)-but-1-enyl]-3,3-dimethyl-2-oxo-pyrrolidin-1-yl}-heptanoic acid (59), MS: m/z 432 (M⁺¹);

{2-[3-(4-Methoxybenzyl)-phenyl]-2-oxo-ethyl}phosphonic acid dimethyl ester in step 4 gives 7-((R)-5-{(E)-3-Hydroxy-3-[3-(4-methoxy-benzyl)-phenyl]-propenyl}-3,3-dimethyl-2-oxo-pyrrolidin-1-yl)-heptanoic acid (60), MS: m/z 494 (M⁺¹); or

[2-(4'-Chloro-2'-methyl-biphenyl-3-yl)-2-oxo-ethyl]phosphonic acid dimethyl ester in step 4 gives 7-{(R)-5-[(E)-3-(4'-Chloro-2'-methyl-biphenyl-3-yl)-3-hydroxy-propenyl]-3,3-dimethyl-2-oxo-pyrrolidin-1-yl}-heptanoic acid (61), MS: m/z 499 (M⁺¹).

Example 7

7-((R)-2-{(E)-3-[3-(3-Fluoro-phenoxy)-phenyl]-3-hydroxy-propenyl}-5-oxo-pyrrolidin-1-yl)-heptanoic Acid (62)

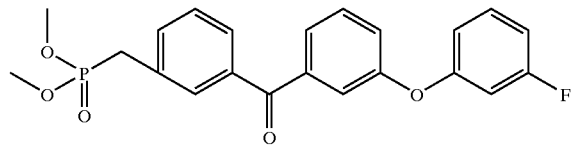

This example illustrates the synthesis of the phosphonate of the above formula by the method described in Scheme B.

Step 1

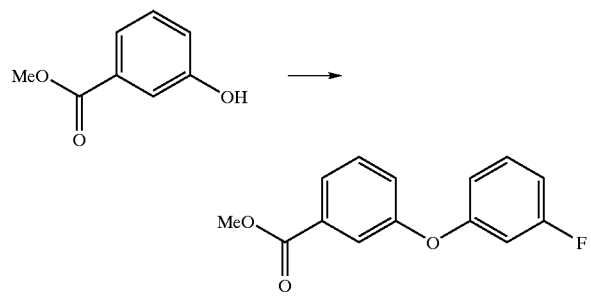

A suspension of methyl 3-hydroxybenzoic acid (5.4 g, 35.5 mmol), 3-fluorophenylboronic acid (5.5 g, 35.5 mmol), cupric acetate (7.1 g, 35.5 mmol), 3 Å molecular sieves (9 g), pyridine (12 mL, 145 mmol) in dichloromethane (220 mL) was stirred at ambient temperature under ambient atmosphere. After 11 days, the mixture was filtered through Celite and the volatiles were removed from the filtrate. The desired ester (3.68 g) was eluted from silica gel column with 5:1 hexane:ethyl acetate and taken onto the next step.

Step 2

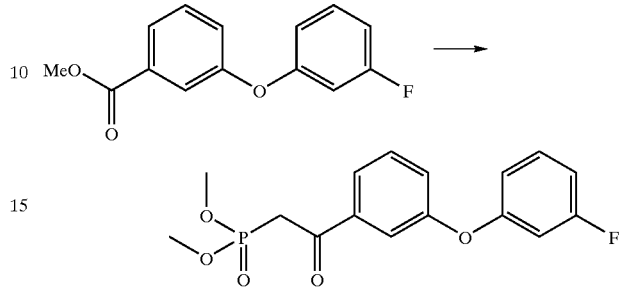

A tetrahydrofuran (100 mL) solution of dimethyl methylphosphonate (4.0 mL, 37.5 mmol) was cooled to −78° C. under argon and treated with normal butyllithium (15.0 mL, 2.5 M hexane solution, 37.5 mmol) and allowed to stir for 45 minutes. The ester obtained from step 1 (4.62 g, 18.7 mmol) was dissolved in tetrahydrofuran (15 mL) and added to the solution above at −78° C. and the resulting mixture was stirred at 0° C. for 1 hour. At which time, the yellow solution was partitioned between aqueous ammonium chloride (100 mL) and ethyl ether (200 mL). The organic portion was washed with fresh water (3×30 mL), then brine, and stored over anhydrous sodium sulfate. Following filtration and removal of the volatiles in vacuo, the desired β-ketophosphonate (5.8 g) was obtained as a viscous oil: ¹H NMR (300 MHz, CDCl₃) □ 7.78 (dt, J=0.6, 0.9, 7.8 Hz, 1 H), 7.63 (t, J=2.1 Hz, 1H), 7.48 (t, J=8.1 Hz, 1 H),7.32–7.26 (m, 2 H), 6.90–6.78 (m, 2 H), 6.70 (dt, J=2.4, 9.9 1 H), 3.80 (d, J=11.2 Hz, 6 H), 3.61 (d, J=22.6, 2 H).

Following the method in Example 1, {2-[3-Fluoro-phenoxy)-phenyl]-2-oxo-ethyl}-phosphonic acid dimethyl ester was used to prepare 7-((R)-2-{(E)-3-[3-(3-Fluoro-phenoxy)-phenyl]-3-hydroxy-propenyl}-5-oxo-pyrrolidin-1-yl)-heptanoic acid (62) (90), MS m/z 456 (M⁺¹).

Similarly replacing 3-fluorophenylboronic acid in Step 1 with appropriately substituted phenylboronic acid, the following compounds of Formula I were prepared:

phenylboronic acid gives 7-((R)-2-{(E)-3-(3-phenoxy)-phenyl-3-hydroxy-propenyl}-5-oxo-pyrrolidin-1-yl)-heptanoic acid (63), MS m/z 438 (M⁺¹);

4-methoxyphenylboronic acid gives 7-((R)-2-{(E)-3-Hydroxy-3-[3-(4-methoxy-phenoxy)-phenyl]-propenyl}-5-oxo-pyrrolidin-1-yl)-heptanoic acid (64), MS: m/z 468 (M⁺¹);

4-fluorophenylboronic acid (with a susequent hydrogenation at 1 atm hydrogen gas and 10% palladium on carbon) gives 7-((S)-2-{(E)-3-Hydroxy-3-[3-(4-fluoro-phenoxy)-phenyl]-propyl}-5-oxo-pyrrolidin-1-yl)-heptanoic acid (65), MS: 458 m/z (M⁺¹);

m-tolylboronic acid gives 7-((R)-2-[(E)-3-Hydroxy-3-(3-m-tolyloxy-phenyl)-propenyl]-5-oxo-pyrrolidin-1-yl)-heptanoic acid (66), MS: m/z 452 (M⁺¹);

3-methoxyphenylboronic acid gives 7-((R)-2-{(E)-3-Hydroxy-3-[3-(3-methoxy-phenoxy)-phenyl]-propenyl}-5-oxo-pyrrolidin-1-yl)-heptanoic acid (67), MS: m/z 468 (M⁺¹);

4-trifluoromethylphenylboronic acid gives 7-((R)-2-{(E)-3-Hydroxy-3-[3-(4-trifluoromethyl-phenoxy)-phenyl]-propenyl}-5-oxo-pyrrolidin-1-yl)-heptanoic acid (68), MS: m/z 506 (M⁺¹);

o-tolylboronic acid gives 7-((R)-2-[(E)-3-Hydroxy-3-(3-o-tolyloxy-phenyl)-propenyl]-5-oxo-pyrrolidin-1-yl)-heptanoic acid (69), MS: m/z 452 ($M^{+1}$);

3-trifluoromethylphenylboronic acid gives 7-((R)-2-{(E)-3-Hydroxy-3-[3-(3-trifluoromethyl-phenoxy)-phenyl-]-propenyl}-5-oxo-pyrrolidin-1-yl)-heptanoic acid (70), MS: m/z 506 ($M^{+1}$);

2-methoxyphenylboronic acid gives 7-((R)-2-{(E)-3-Hydroxy-3-[3-(2-methoxy-phenoxy)-phenyl]propenyl}-5-oxo-pyrrolidin-1-yl)-heptanoic acid (71), MS: m/z 468 ($M^{+1}$);

p-tolylboronic acid gives 7-((R)-2-[(E)-3-Hydroxy-3-(3-p-tolyloxy-phenyl)-propenyl]-5-oxo-pyrrolidin-1-yl)-heptanoic acid (72), MS: m/z 452 ($M^{+1}$);

4-fluorophenylboronic acid gives 7-((R)-2-{(E)-3-[3-(4-Fluoro-phenoxy)-phenyl]-3-hydroxy-propenyl}-5-oxo-pyrrolidin-1-yl)-heptanoic acid (73), MS: m/z 456 ($M^{+1}$);

4-chlorophenylboronic acid gives 7-((R)-2-{(E)-3-[3-(4-chloro-phenoxy)-phenyl]-3-hydroxy-propenyl}-5-oxo-pyrrolidin-1-yl)-heptanoic acid (74), MS: m/z 473 ($M^{+1}$); or 3-chlorophenylboronic acid gives 7-((R)-2-{(E)-3-[3-(3-chloro-phenoxy)-phenyl]-3-hydroxy-propenyl}-5-oxo-pyrrolidin-1-yl)-heptanoic acid (75), MS: m/z 473 ($M^{+}$).

Example 8

4-{2-[(R)-2-((E)-3-Hydroxy-oct-1-enyl)-5-oxo-pyrrolidin-1-yl]-ethyl}-benzoic Acid (76)

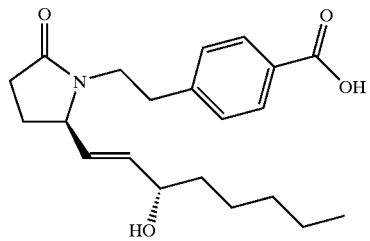

Step 1

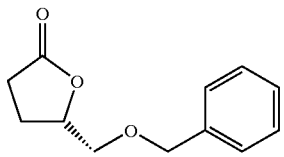

40 mL of DMF were added to 1.27 g (31.67 mmol, 60% dispersion in mineral oil) NaH and 5.26 g (31.67 mmol) KI at 0° C. under $N_2$. A solution of 3.50 g (30.16 mmol) of (S)-(+)-dihydro-5-hydroxymethyl-2(3H)furanone (Aldrich) in 15 mL of DMF was then added drop wise. Slurry was allowed to warm to room temperature and stir for 2.5 hours, 5.4 mL (45.24 mmol) benzyl bromide were then added drop wise and mixture was heated to 50° C. and allowed to stir for 16 hours. Reaction was partitioned between 250 mL saturated $NH_4Cl_{(aq)}$ and 250 mL ethyl acetate/hexane (60%). Organic layer was washed with water (3×200 mL), 200 mL brine, dried over Magnesium Sulfate and concentrated under reduced pressure. Crude residue was purified via chromatography, eluting with 35% ethyl acetate/hexane yielding 3.37 g (16.34 mmol, 54% yield) (S)—O-Benzyl-dihydro-5-hydroxymethyl-2(3H)furanone as a yellow oil.

Step 2

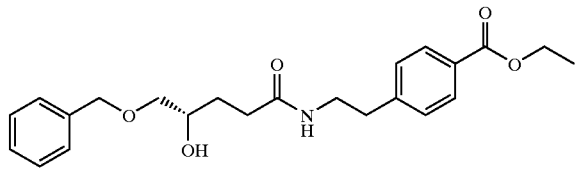

1.98 g (9.59 mmol) (S)—O-Benzyl-dihydro-5-hydroxymethyl-2(3H)furanone and 3.14 g (16.25 mmol) ethyl p-aminoethylbenzoate were dissolved in 50 mL THF and stirred at 50° C. for 20 hours. Reaction was concentrated and crude residue purified via chromatography, eluting with 50% ethyl acetate/hexane yielding 2.24 g (5.61 mmol, 58% yield) N'-[2-(4-carboethoxyphenyl)ethyl]-5-benzyloxy-4-hydroxypentanamide as a white solid.

Step 3

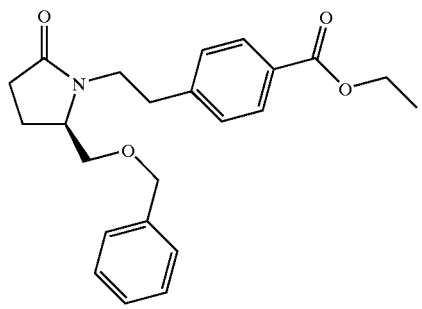

2.24 g (5.61 mmol) N'-[2-(4-carboethoxyphenyl)ethyl]-5-benzyloxy-4-hydroxypentylamide were dissolved in 40 mL THF and 1.17 mL (8.43 mmol) triethyl amine and stirred for 10 minutes. 0.57 mL (7.30 mmol) Methanesulfonyl chloride were then added dropwise and the reaction mixture was allowed to stir for 2.5 hours, the precipitate was filtered off and residue rinsed with 3 mL THF. To the filtrate was added 1.33 g (11.85 mmol) t-BuOK and reaction was stirred at room temperature for 2 hours. Upon completion reaction was partitioned between 200 mL saturated $NH_4Cl_{(aq)}$ and 250 mL ethyl acetate. Organic layer was washed with 100 mL $H_2O$, 200 mL brine, dried over $MgSO_4$, and concentrated under reduced pressure. Crude oil was purified via chromatography, eluting with 1% $MeOH/CH_2Cl_2$ yielding 1.78 g (4.69 mmol, 83% yield) of (R)-N'-[2-(4-carboethoxyphenyl)ethyl]-5-benzyloxymethyl-2-pyrrolidinone as a clear oil.

Step 4

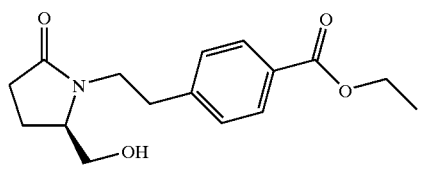

1.78 g (4.69 mmol) (R)-N'-[2-(4-Carboethoxyphenyl)ethyl]-5-benzyloxymethyl-2-pyrrolidinone were dissolved in 20 mL ethanol. Reaction was sparged with Argon gas before adding 0.63 g 10% Pd/C and 0.095 g (0.55 mmol) p-toluenesulfonic acid. Reaction vessel was then evacuated and purged with hydrogen gas and allowed to stir at room temperature 4 hours and then filtered through Celite®. The filtrate was concentrated, resulting in 1.35 g (4.63 mmol, 98% yield) of (R)-N'-[2-(4-carboethoxyphenyl)ethyl]-5-hydroxymethyl-2-pyrrolidinone as clear and colorless oil.

Step 5

The alcohol obtained in the above step is then converted into the desired ester and acid by steps described in Scheme A above while utilizing the combination of catalytic amounts of (R)-2-methyl-"CBS"-oxazaborolidine with stoichiometric borane-dimethyl sulfide as described by E. J. Corey, et al., *J. Am. Chem. Soc.* 1987, 109, 7925–7926 to produce the alcohol-ester shown: $[(M+H)^+=388]$.

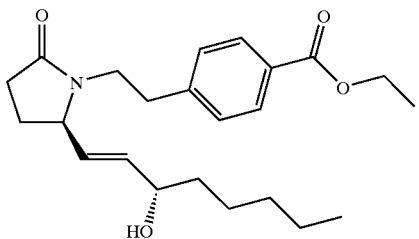

Hydrolysis of above ester as previously described gives the benzoid acid (76), MS: m/z 360 (M+1) as a white powder.

Replacing ethyl-p-aminoethylbenzoate in Step 2, following compounds of Formula I were prepared:

methyl p-(3-aminopropyl)benzoate gives 4-{3-[(R)-2-((E)-3-Hydroxy-oct-1-enyl)-5-oxo-pyrrolidin-1-yl]-propyl}-benzoic acid (77), MS: m/z 374 $(M+1)^+$;

methyl m-(3-aminopropyl)benzoate gives 3-{3-[(R)-2-((E)-3-Hydroxy-oct-1-enyl)-5-oxo-pyrrolidin-1-yl]-propyl}-benzoic acid (78), MS: m/z 374 $(M+1)^+$;

methyl o-(3-aminopropyl)benzoate gives 2-{3-[(R)-2-((E)-3-Hydroxy-oct-1-enyl)-5-oxo-pyrrolidin-1-yl]-propyl}-benzoic acid (79), MS: m/z 374 $(M+1)^+$;

1-(2-aminoethyl)-1H-pyrazole-4-carboxylic acid gives 1-{2-[(R)-2-((E)-3-Hydroxy-oct-1-enyl)-5-oxo-pyrrolidin-1-yl]-ethyl}-1H-pyrazole-4-carboxylic acid (80), MS: m/z 349 $(M+1)^+$.

Alternatively starting with [2-(4'chloro-2'-methyl-biphen-3-yl)-2-oxo-ethyl]-phosphonic acid dimethyl followed by reduction with 1 atm hydrogen gas, catalytic 10% palladium on carbon in EtOAc, 1.5 h, and then subjected to reduction conditions described by E. J. Corey, et al., *J. Am. Chem. Soc.* 1987, 109, 7925–7926 using the (S)-2-methyl-CBS catalyst, 1 M toluene solution from Aldrich, gives 4-(2-{(S)-2-[(R)-3-(4'-Chloro-2'-methyl-biphenyl-3-yl)-3-hydroxy-propyl]-5-oxo-pyrrolidin-1-yl}-ethyl)-benzoic acid (81), MS: m/z 493 $(M+1)^+$; or using ethyl 5-(2-aminoethyl)-thiophene-2-carboxylic acid gives 5-[(R)-2-((E)-3-Hydroxy-oct-1-enyl)-5-oxo-pyrrolidin-1-yl]-ethyl)-thiophene-2-carboxylic acid (82), MS: m/z 366 $(M+1)^+$.

Example 9

The following are representative pharmaceutical formulations containing a compound of Formula I.

Tablet formulation
The following ingredients are mixed intimately and pressed into single scored tablets.

| Ingredient | Quantity per tablet, mg |
|---|---|
| compound of this invention | 400 |
| cornstarch | 50 |
| croscaramellose sodium | 25 |
| lactose | 120 |
| magnesium stearate | 5 |

Capsule formulation
The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension formulation
The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Injectable formulation
The following ingredients are mixed to form an injectable formulation.

| Ingredient | Amount |
|---|---|
| compound of this invention | 0.4 mg |
| sodium acetate buffer solution, 0.4 M | 2.0 mL |
| HCl (1 N) or NaOH (1 N) | q.s. to suitable pH |
| water (distilled, sterile) | q.s. to 20 mL |

Example 10

Functional Activity of $EP_4$ (or $EP_2$) Receptor by a Luciferase Assay

The receptor expressed $EP_4$ (or $EP_2$) cells were subcultured in F12 (Gibco, BRL) media containing 10% FBS (Gibco, BRL), and 25 mM Hepes to 96-well plates (Packard) and incubated overnight. The culture media was removed in the next morning. The cells were washed twice with Hanks buffer, and re-furnish with F12 media containing 0.1% BSA. After pre-incubated the culture for one and half to three hours, compounds of interest were added to culture and the incubation was continued for another three hours. The luciferase activities in the cells were measured by LucLite, which is manufactured by Packard, with the protocol recommended by Packard.

Example 11

Competitive Binding Assay of [$^3$H]$PGE_2$ to $rEP_1$ or $rEP_3$ Receptor

The cells were maintained in culture then harvested upon confluency. The membrane was prepared by two times of centrifugation (12,000× g for 15 min) following lysis of cells by polytron homogenization of 15 sec. in 10 volume of 20 mM Hepes pH 7.4 containing 1 mM EDTA, 10 mM $MgCl_2$, 20 uM indomethacin at 4° C. The inhibition of compounds in the [$^3$H]$PGE_2$ binding assay were performed in the previously described buffer containing 3 nM [$^3$H]PGE2, 2%

DMSO, various concentrations of compound and 25 μg of protein from the membrane fraction. Incubations were conducted for 1 hr at 30° C. prior to separation of the bound and free radioligand by rapid filtration. Residual [$^3$H]PGE$_2$ bound to the filter was quantitated by liquid scintillation counting. The Ki of a compound was calculated by the program of one site binding calculation of Prism. Representative Data is Shown Below

| Compound | EP$_1$, K$_i$ (μM) | EP$_2$, K$_i$ (μM) | EP$_3$, K$_i$ (μM) | EP$_4$, K$_i$ (μM) |
| --- | --- | --- | --- | --- |
| 50 | ND | 26 | >100 | .008 |
| 55 | >100 | >100 | >100 | .007 |
| 59 | >ND | >100 | >100 | 0.07 |
| 74 | ND | 22.9 | 47 | 0.01 |
| 76 | NT | 0.13 | 11 | 0.0012 |
| 81 | NT | 5.1 | 54 | 0.00094 |
| 82 | NT | 3.7 | >100 | 0.069 |

ND = not determined.

Example 12

Bone Mass Density Assay

The compounds of this invention are evaluated for their effect on bone mass in ovariectomized rats.

Adult Sprague-Dawley or Wistar Hanover female rats are either sham operated or ovariectomized by Charles River. On receipt, rats are housed in pairs in an environmentally controlled room and acclimatized for at least one week. Animals are pair fed while were housed on site.

Test compound is administered subcutaneously once a day started from 20 days post surgery for 5 weeks in 10% EtOH/saline or 20 mM phosphate buffer.

Before the treatment and at the end of the treatment, rats are scanned using High Resolution Software Package on a Hologic QDR-4500 Bone Densitometer to measure the bone mineral density (BMD). Scans are then analyzed using regions of interest, as designated below: whole femur, proximal femur, femur diaphysis, distal femur, distal femur metaphysis, proximal tibia, proximal tibia metaphysis, L2-L4-vertebrae, L5 vertebrae.

For a verification of the effect of ovariectomy on bone mass, the sham and OVX of like vehicle groups are compared using a students t-test. The OVX groups are compared by one way analysis of variance (ANOA), followed by Fisher's LSD to compare each treatment group to vehicle when the overall effect was statistically significant. The data could be ranked prior to the above analysis and corresponding non-parametric analysis were performed (Wilcoxon rank-sum test or Kruskal-Wallis).

What is claimed is:

1. A compound comprising Formula I:

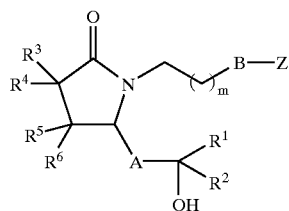

I wherein:

A is —CH$_2$—CH$_2$—, or —CH═CH—;

B is absent, aryl, or heteroaryl;

Z is —C(O)OR', —C(O)NR'R", —C(O)NSO$_2$R', —PR'(O)(OR'), —PO(OR')$_2$, or tetrazol-5-yl;

wherein R' and R" are independently from each other hydrogen or (C$_1$–C$_6$)alkyl;

m is 1, 2, 3, 4, 5, or 6;

R$^1$ is alkyl, alkenyl, alkynyl, cycloalkylalkyl, heterocyclylalkyl, aryl, arylalkyl or heteroaryl;

provided that R$^1$ is alkyl, alkenyl, alkynyl, cycloalkylalkyl, heterocyclylalkyl, aryl, arylalkyl or heteroaryl, when B is aryl or heteroaryl and R$^3$, R$^4$, R$^5$ and R$^6$ are not simultaneously hydrogen, and R$^1$ is heterocyclylalkyl, aryl, or heteroaryl when B is absent and R$^3$, R$^4$, R$^5$ and R$^6$ are simultaneously hydrogen;

R$^2$ is hydrogen or (C$_1$–C$_6$)alkyl, (C$_1$–C$_6$)alkenyl, or (C$_1$–C$_6$)alkynyl;

R$^3$, R$^4$, R$^5$ and R$^6$ are each independently from each other hydrogen or (C$_1$–C$_6$) alkyl; or R$^3$ and R$^4$, R$^5$ and R$^6$ or R$^3$ and R$^5$ taken together with the atom to which they are attached may form a (C$_3$–C$_7$) alkyl ring; or a pharmaceutically acceptable salt or solvate, single isomer or racemic or non-racemic mixture of isomers thereof.

2. The compound of claim 1, wherein B is absent and R$^1$ is an aryl optionally substituted with a substituent selected from the group consisting of trifluoromethyl, halogen, —Y—R$^a$; —Y—OR$^a$, and —Y—C(O)R$^a$; Y is a bond or a (C$_1$–C$_3$)alkylene group, and R$^a$ is (C$_1$–C$_6$)alkyl, aryl, heterocyclyl, heteroaryl, or heterocyclyl.

3. The compound of claim 2, wherein R$^1$ is an unsubstituted phenyl.

4. The compound of claim 2, wherein R$^1$ is a phenyl substituted with a substituent selected from the group consisting of trifluoromethyl, halogen, —Y—R$^a$; —Y—OR$^a$, and —Y—C(O)R$^a$; Y is a bond or a (C$_1$–C$_3$)alkylene group, and R$^a$ is (C$_1$–C$_6$)alkyl, aryl, heterocyclyl, heteroaryl, or heterocyclyl.

5. The compound of claim 4, wherein R$^a$ is a phenyl optionally substituted with a substituent selected from the group consisting of (C$_1$–C$_6$)alkyl, (C$_1$–C$_6$)alkoxy, trifluoromethyl, and halogen.

6. The compound of claim 2, wherein R$^1$ is a phenyl substituted with at least one —Y—R$^a$, wherein Y is a bond or a (C$_1$–C$_3$)alkylene group; R$^a$ is a phenyl optionally substituted with a substituent selected from the group consisting of (C$_1$–C$_6$)alkyl, (C$_1$–C$_6$)alkoxy, trifluoromethyl and halogen.

7. The compound of claim 2, wherein R$^1$ is a phenyl substituted with at least one —Y—R$^a$, wherein Y is a bond or a (C$_1$–C$_3$)alkylene group; R$^a$ is an optionally substituted heteroaryl.

8. The compound of claim 2, wherein R$^1$ is a phenyl substituted with at least one —Y—OR$^a$, wherein Y is a bond or a (C$_1$–C$_3$)alkylene group; and R$^a$ is a phenyl substituted with a substituent selected from the group consisting of (C$_1$–C$_6$)alkyl, (C$_1$–C$_6$)alkoxy, trifluoromethyl, and halogen.

9. The compound of claim 2, wherein R$^1$ is a phenyl susbstituted with at least one —Y—C(O)R$^a$, wherein Y is a bond or a (C$_1$–C$_3$)alkylene group; and R$^a$ is phenyl optionally substituted with at least one substituent selected from the group consisting of (C$_1$–C$_6$)alkyl, (C$_1$–C$_6$)alkoxy, trifluoromethyl, and halogen.

10. The compound of claim 1, wherein B is absent and R$^1$ is heteroaryl.

11. The compound of claim 10, wherein R$^1$ is a heteroaryl substituted with a substituent is selected from the group consisting of trifluoromethyl, halogen, —Y—R$^a$, —Y—OR$^a$ and —Y—C(O)R$^a$, wherein Y is a bond or a (C$_1$-C$_3$)alkylene group; and R$^a$ is (C$_1$-C$_6$)alkyl, aryl, heterocyclyl, heteroaryl, or heterocyclyl.

12. The compound of claim 1, wherein B is absent, R$^3$ and R$^4$ are (C$_1$-C$_6$)alkyl.

13. The compound of claim 12, wherein R$^1$ is a phenyl optionally substituted with a substituent selected from the group consisting of trifluoromethyl, halogen, —Y—R$^a$, —Y—OR$^a$, and —Y—C(O)R$^a$; Y is a bond or a (C$_1$-C$_3$) alkylene group; and R$^a$ is (C$_1$-C$_6$)alkyl, aryl, heterocyclyl, heteroaryl, or heterocyclyl.

14. The compound of claim 12, wherein R$^1$ is a heteroaryl optionally substituted with a substituent selected from the group consisting of trifluoromethyl, halogen —Y—R$^a$, —Y—OR$^a$, and —Y—C(O)R$^a$; wherein Y is a bond or a (C$_1$-C$_3$)alkylene group; and R$^a$ is (C$_1$-C$_6$)alkyl, aryl, heterocyclyl, heteroaryl, or heterocyclyl.

15. The compound of claim 14, wherein R$^1$ is alkyl or cycloalkylalkyl.

16. The compound of claim 15, wherein A is —CH$_2$—CH$_2$.

17. The compound of claim 1, wherein B is absent and A is —CH$_2$—CH$_2$.

18. The compound of claim 17, wherein B is absent and R$^1$ is a phenyl optionally subsituted with a substituent selected from the group consisting of trifluoromethyl, halogen, —Y—R$^a$, —Y—OR$^a$, and —Y—C(O)R$^a$, wherein Y is a bond or a (C$_1$-C$_3$)alkylene group; and R$^a$ is (C$_1$-C$_6$) alkyl, aryl, heterocyclyl, heteroaryl, or heterocyclyl.

19. The compound according to claim 1, wherein B is an aryl, m is one or two and R$^1$ is alkyl, aryl or heteroaryl.

20. The compound of claim 19, wherein R$^1$ is an optionally substituted phenyl.

21. The compound according to claim 20, wherein R$^1$ is alkyl.

22. The compound of claim 1, wherein B is a heteroaryl, m is one or two and R$^1$ is alkyl.

23. A pharmaceutical composition comprising a therapeutically effective amount of a compound of claim 1 in admixture with at least one suitable carrier diluent or excipient.

24. A method of treatment of a disease in a mammal treatable by administration of a selective EP$_4$ prostaglandin agonist comprising administration to the mammal a therapeutically effective amount of a compound of claim 1.

25. The method of claim 24, wherein the disease is associated with bone disorders.

26. A process for preparing a compound according to claim 1, which comprises:
reacting a compound of general formula a:

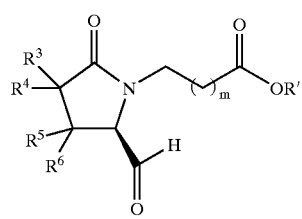

a wherein m, R$^3$, R$^4$, R$^5$, and R$^6$ are as defined in claim 1, with a phosphonate of general formula m:

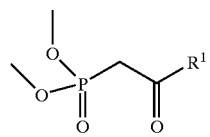

m wherein R$^1$ is as defined in claim 1, followed by reduction and optional hydrolysis to give a compound of Formula I:

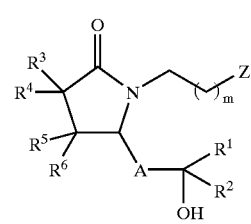

I wherein R$^2$ is hydrogen and m, R$^1$, R$^3$, R$^4$, R$^5$, and R$^6$ are as defined in claim 1.

27. A process for preparing a compound according to claim 1, which comprises:
reacting a compound of general formula:

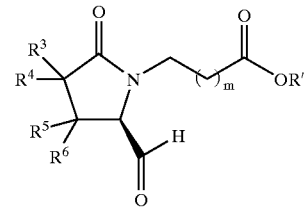

wherein m, R$^3$, R$^4$, R$^5$ and R$^6$ are as defined in claim 1, with a phosphonate of general formula m:

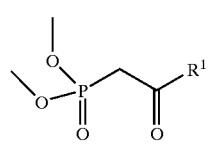

m wherein R$^1$ is as defined in claim 1, followed by reaction with an organometallic compound of formula R$^2$M, wherein M is a metal or magnesium halide, and R$^2$ is as defined in claim 1;
and optional hydrolysis to give a compound of Formula I:

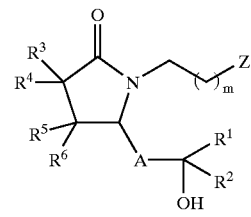

I wherein A, m, R$^1$, R$^2$, R$^3$, R$^4$, R$^5$, R$^6$ and Z are as defined in claim 1.

28. A process for preparing a compound according to claim 1, which comprises:

a) reacting a compound of formula:

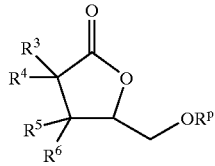

wherein $R^p$ is a protecting group, $R^3$, $R^4$, $R^5$ and $R^6$ are as defined in claim 1, with an amine of formula:

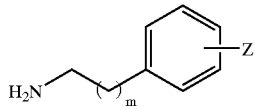

wherein m and Z are as defined in claim 1, followed by deprotection of the protected hydroxyl group to obtain a compound of formula:

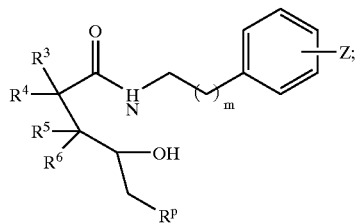

b) activating the hydroxy group in the compound obtained above and contacting the resulting compound with a base followed by deprotection of the protected hydroxyl to obtain a compound of formula:

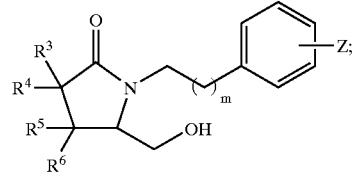

c) oxidizing the compound obtained in step b) to an aldehyde of formula:

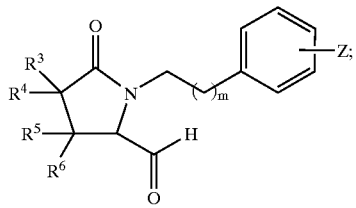

d) reacting the above aldehyde with a phosphonate of general formula m:

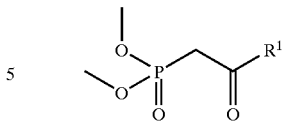

wherein $R^1$ is as defined in claim 1 to obtain compound of formula:

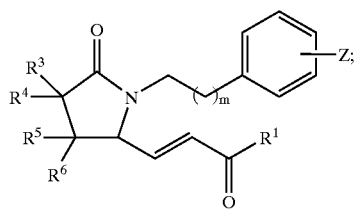

e) reacting the compound obtained in step d) with an organometallic compound of formula $R^2M$, wherein M is a metal or magnesium halide, and $R^2$ is as defined in claim 1; and f) optionally hydrolysing the ester to give a compound of Formula I.

29. A compound according to claim 1 selected from the group consisting of:

7-{(R)-2-[(E)-3-(3-Benzyl-phenyl)-3-hydroxy-propenyl]-5-oxo-pyrrolidin-1-yl}-heptanoic acid;

7-[(R)-2-((E)-3-hydroxy-3-naphthalen-2-yl-propenyl)-5-oxo-pyrrolidin-1-yl]-heptanoic acid;

7-{(R)-2-[(E)-3-hydroxy-3-(3-phenoxy-phenyl)-propenyl]-5-oxo-pyrrolidin-1-yl}-heptanoic acid;

7-[(R)-2-((E)-3-hydroxy-3-phenyl-propenyl)-5-oxo-pyrrolidin-1-yl]-heptanoic acid 7-{(R)-2-[(E)-3-hydroxy-3-(3-methoxy-phenyl)-propenyl]-5-oxo-pyrrolidin-1-yl}-heptanoic acid;

7-{(R)-2-[(E)-3-hydroxy-3-(4-phenoxy-phenyl)-propenyl]-5-oxo-pyrrolidin-1-yl}-heptanoic acid;

7-{(R)-2-[(E)-3-(3-ethoxy-phenyl)-3-hydroxy-propenyl]-5-oxo-pyrrolidin-1-yl}-heptanoic acid;

7-{(R)-2-[(E)-3-(3-ethyl-phenyl)-3-hydroxy-propenyl]-5-oxo-pyrrolidin-1-yl}-heptanoic acid;

7-((R)-2-{(E)-3-Hydroxy-3-[3-(morpholine-4-sulfonyl)-phenyl]-propenyl}-5-oxo-pyrrolidin-1-yl)-heptanoic acid;

7-{(R)-2-[(E)-3-(3-Bromo-phenyl)-3-hydroxy-propenyl]-5-oxo-pyrrolidin-1-yl}-heptanoic acid;

7-(R)-{2-[(E)-3-Hydroxy-3-(3-hydroxy-phenyl)-propenyl]-5-oxo-pyrrolidin-1-yl}-heptanoic acid;

7-{(R)-2-[(E)-3-Hydroxy-3-(3-pyrrol-1-ylmethyl-phenyl)-propenyl]-5-oxo-pyrrolidin-1-yl}-heptanoic acid;

7-{(R)-2-[(E)-3-Hydroxy-3-(3-pyrazol-1-ylmethyl-phenyl)-propenyl]-5-oxo-pyrrolidin-1-yl}-heptanoic acid;

7-{(R)-2-[(E)-3-Hydroxy-3-(3-methoxymethyl-phenyl)-propenyl]-5-oxo-pyrrolidin-1-yl}-heptanoic acid;

7-{(R)-2-[(E)-3-(3-Cyclopentyloxy-phenyl)-3-hydroxy-propenyl]-5-oxo-pyrrolidin-1-yl}-heptanoic acid;

7-{(R)-2-[(E)-3-Hydroxy-3-(3-trifluoromethyl-phenyl)-propenyl]-5-oxo-pyrrolidin-1-yl}-heptanoic acid;

7-{(S)-2-[(R)-3-Hydroxy-3-(3-trifluoromethyl-phenyl)-propyl]-5-oxo-pyrrolidin-1-yl}-heptanoic;

7-{(R)-2-[(E)-3-Hydroxy-3-(3-phenoxymethyl-phenyl)-propenyl]-5-oxo-pyrrolidin-1-yl-heptanoic acid;

7-{(R)-2-[(E)-3-Hydroxy-3-(3-phenoxymethyl-phenyl)-propenyl]-5-oxo-pyrrolidin-1-yl}-heptanoic acid methyl ester;

7-((R)-2-{(E)-3-Hydroxy-3-[3-(1-methyl-1H-pyrrol-2-yl)-phenyl]-propenyl}-5-oxo-pyrrolidin-1-yl)-heptanoic acid;

7-((R)-2-{(E)-3-Hydroxy-3-[3-(1-methyl-1H-pyrrol-2-yl)-phenyl]-propenyl}-5-oxo-pyrrolidin-1-yl)-heptanoic acid methyl ester;

7-{(R)-2-[(E)-3-(3-Butoxy-phenyl)-3-hydroxy-propenyl]-5-oxo-pyrrolidin-1-yl}-heptanoic acid;

7-{(R)-2-[(E)-3-(3-Benzyloxy-phenyl)-3-hydroxy-propenyl]-5-oxo-pyrrolidin-1-yl}-heptanoic acid;

7-{(R)-2-[(E)-3-(2-chlorobenzyloxy)-phenyl)-3-hydroxy-propenyl]-5-oxo-pyrrolidin-1-yl}-heptanoic acid;

7-[(R)-2-((E)-3-Biphenyl-2-yl-3-hydroxy-propenyl)-5-oxo-pyrrolidin-1-yl]-heptanoic acid;

7-((R)-2-{(E)-3-Hydroxy-3-[3-(2-morpholin-4-yl-ethoxy)-phenyl]-propenyl}-5-oxo-pyrrolidin-1-yl)-heptanoic acid;

7-((R)-2-(E)-3-Hydroxy-3-[3-(methyl-phenyl-amino)-phenyl]-propenyl}-5-oxo-pyrrolidin-1-yl)-heptanoic acid;

7-((R)-2-{(E)-3-Hydroxy-3-[3-(methyl-o-tolyl-amino)-phenyl]-propenyl}-5-oxo-pyrrolidin-1-yl)-heptanoic acid;

7-{(R)-2-[(E)-3-Hydroxy-3-(3-phenethyloxy-phenyl)-propenyl]-5-oxo-pyrrolidin-1-yl}-heptanoic acid;

7-[(R)-2-((E)-3-Hydroxy-3-{3-[2-(2-oxo-pyrrolidin-1-yl)-ethoxy]-phenyl}-propenyl)-5-oxo-pyrrolidin-1-yl]-heptanoic acid;

7-((R)-2-{(E)-3-[3-(2-tert-butoxy-ethoxy)-phenyl]-3-hydroxy-propenyl}-5-oxo-pyrrolidin-1-yl)-heptanoic acid;

7-{(R)-2-[(E)-3-Hydroxy-3-(3-indol-1-yl-phenyl)-propenyl]-5-oxo-pyrrolidin-1-yl}-heptanoic acid;

7-{(R)-2-[(E)-3-Hydroxy-3-((Z)-3-propenyl-phenyl)-propenyl]-5-oxo-pyrrolidin-1-yl}-heptanoic acid;

7-{(R)-2-[(E)-3-Hydroxy-3-(3-propyl-phenyl)-propenyl]-5-oxo-pyrrolidin-1-yl}-heptanoic acid;

7-{(R)-2-[(E)-3-(3-Dimethylcarbamoyl-phenyl)-3-hydroxy-propenyl]-5-oxo-pyrrolidin-1-yl}-heptanoic acid;

7-((R)-2-{(E)-3-Hydroxy-3-[3-(tetrahydro-pyran-4-ylidenemethyl)-phenyl]-propenyl}-5-oxo-pyrrolidin-1-yl)-heptanoic acid;

7-((R)-2-{(E)-3-Hydroxy-3-[3-(tetrahydro-pyran-4-ylmethyl)-phenyl]-propenyl}-5-oxo-pyrrolidin-1-yl)-heptanoic acid;

7-((R)-2-{(E)-3-Hydroxy-3-[3-(4-methoxy-benzyl)-phenyl]-propenyl}-5-oxo-pyrrolidin-1-yl)-heptanoic acid;

7-{(R)-2-[(E)-3-Hydroxy-3-(5-trifluoromethyl-furan-2-yl)-propenyl]-5-oxo-pyrrolidin-1-yl}-heptanoic acid;

7-{(R)-2-[(E)-3-Hydroxy-3-(3-methoxymethyl-phenyl)-propenyl]-5-oxo-pyrrolidin-1-yl}-heptanoic acid;

7-((R)-2-{(E)-3-[3-(dimethoxy-phenyl-methyl)-phenyl]-3-hydroxy-propenyl}-5-oxo-pyrrolidin-1-yl)-heptanoic acid;

7-{(R)-2-[(E)-3-(3-Benzoyl-phenyl)-3-hydroxy-propenyl]-5-oxo-pyrrolidin-1-yl}-heptanoic acid;

7-[(R)-2-((E)-3-Hydroxy-3-{3-[1-(4-methoxy-phenyl)-methanoyl]-phenyl}-propenyl)-5-oxo-pyrrolidin-1-yl]-heptanoic acid;

7-{(R)-2-[(E)-3-Hydroxy-3-(2'-methyl-biphenyl-3-yl)-propenyl]-5-oxo-pyrrolidin-1-yl}-heptanoic acid;

7-[(R)-2-((E)-3-Biphenyl-3-yl-3-hydroxy-propenyl)-5-oxo-pyrrolidin-1-yl]-heptanoic acid;

7-{(R)-2-[(E)-3-(2'-Ethoxy-biphenyl-3-yl)-3-hydroxy-propenyl]-5-oxo-pyrrolidin-1-yl}-heptanoic acid;

7-{(R)-2-[(E)-3-(2'-Chloro-biphenyl-3-yl)-3-hydroxy-propenyl]-5-oxo-pyrrolidin-1-yl}-heptanoic acid;

7-{(R)-2-[(E)-3-(4'-Chloro-biphenyl-3-yl)-3-hydroxy-propenyl]-5-oxo-pyrrolidin-1-yl}-heptanoic acid;

7-{(R)-2-[(E)-3-(3'-Chloro-biphenyl-3-yl)-3-hydroxy-propenyl]-5-oxo-pyrrolidin-1-yl}-heptanoic acid;

7-{(R)-2-[(E)-3-(4'-Chloro-2'-methyl-biphenyl-3-yl)-3-hydroxy-propenyl]-5-oxo-pyrrolidin-1-yl}-heptanoic acid;

7-{(R)-2-[(E)-3-(4'-Hydroxy-2'-methyl-biphenyl-3-yl)-3-hydroxy-propenyl]-5-oxo-pyrrolidin-1-yl}-heptanoic acid;

7-{(R)-2-[(E)-3-(4'-Chloro-2'-methyl-biphenyl-3-yl)-3-hydroxy-propyl]-5-oxo-pyrrolidin-1-yl}-heptanoic acid;

7-{(S)-2-[(R)-3-Hydroxy-3-(4'-hydroxy-2'-methyl-biphenyl-3-yl)-propyl]-5-oxo-pyrrolidin-1-yl}-1-heptanoic;

7-{(R)-2-[(E)-3-(6,2'-Dimethyl-biphenyl-3-yl)-3-hydroxy-propenyl]-5-oxo-pyrrolidin-1-yl}-heptanoic acid;

7-{(S)-2-[3-(1-Benzyl-1H-pyrazol-4-yl)-3-hydroxy-propyl]-5-oxo-pyrrolidin-1-yl}-heptanoic acid;

7-{(S)-2-[3-Hydroxy-3-(5-o-tolyl-furan-2-yl)-propyl]-5-oxo-pyrrolidin-1-yl}-heptanoic acid;

7-{(R)-5-[(E)-3-Hydroxy-3-(5-trifluoromethyl-furan-2-yl)-propenyl]-3,3-dimethyl-2-oxo-pyrrolidin-1-yl}-heptanoic acid;

7-[(R)-5-((E)-3-hydroxy-oct-1-enyl)-3,3-dimethyl-2-oxo-pyrrolidin-1-yl]-heptanoic acid;

7-[2-((E)-3-hydroxy-oct-1-enyl)-3,3-dimethyl-5-oxo-pyrrolidin-1-yl]-heptanoic acid;

7-[(R)-5-((S)-(E)-5-Cyclobutyl-3-hydroxy-pent-1-enyl)-3,3-dimethyl-2-oxo-pyrrolidin-1-yl]-heptanoic acid;

7-{(R)-5-[(E)-3-Hydroxy-4-(3-methoxymethyl-phenyl)-but-1-enyl]-3,3-dimethyl-2-oxo-pyrrolidin-1-yl}-heptanoic acid;

7-((R)-5-{(E)-3-Hydroxy-3-[3-(4-methoxy-benzyl)-phenyl]-propenyl}-3,3-dimethyl-2-oxo-pyrrolidin-1-yl)-heptanoic acid;

7-{(R)-5-[(E)-3-(4'-Chloro-2'-methyl-biphenyl-3-yl)-3-hydroxy-propenyl]-3,3-dimethyl-2-oxo-pyrrolidin-1-yl}-heptanoic acid;

7-((R)-2-{(E)-3-[3-(3-Fluoro-phenoxy)-phenyl]-3-hydroxy-propenyl}-5-oxo-pyrrolidin-1-yl)-heptanoic acid;

7-((R)-2-{(E)-3-(3-phenoxy)-phenyl-3-hydroxy-propenyl}-5-oxo-pyrrolidin-1-yl)-heptanoic acid;

7-((R)-2-{(E)-3-Hydroxy-3-[3-(4-methoxy-phenoxy)-phenyl]-propenyl}-5-oxo-pyrrolidin-1-yl)-heptanoic acid;

7-((S)-2-{(E)-3-Hydroxy-3-[3-(4-fluoro-phenoxy)-phenyl]-propyl}-5-oxo-pyrrolidin-1-yl)-heptanoic acid;

7-((R)-2-[(E)-3-Hydroxy-3-(3-m-tolyloxy-phenyl)-propenyl]-5-oxo-pyrrolidin-1-yl)-heptanoic acid;

7-((R)-2-{(E)-3-Hydroxy-3-[3-(3-methoxy-phenoxy)-phenyl]-propenyl}-5-oxo-pyrrolidin-1-yl)-heptanoic acid;

7-((R)-2-{(E)-3-Hydroxy-3-[3-(4-trifluoromethyl-phenoxy)-phenyl]-propenyl}-5-oxo-pyrrolidin-1-yl)-heptanoic acid;

7-((R)-2-[(E)-3-Hydroxy-3-(3-o-tolyloxy-phenyl)-propenyl]-5-oxo-pyrrolidin-1-yl)-heptanoic acid;

7-((R)-2-{(E)-3-Hydroxy-3-[3-(3-trifluoromethyl-phenoxy)-phenyl]-propeny}-5-oxo-pyrrolidin-1-yl)-heptanoic acid;

7-((R)-2-{(E)-3-Hydroxy-3-[3-(2-methoxy-phenoxy)-phenyl]-propenyl}-5-oxo-pyrrolidin-1-yl)-heptanoic acid;

7-((R)-2-[(E)-3-Hydroxy-3-(3-p-tolyloxy-phenyl)-propenyl]-5-oxo-pyrrolidin-1-yl)-heptanoic acid;

7-((R)-2-{(E)-3-[3-(4-Fluoro-phenoxy)-phenyl]-3-hydroxy-propenyl}-5-oxo-pyrrolidin-1-yl)-heptanoic acid;

7-((R)-2-{(E)-3-[3-(4-chluoro-phenoxy)-phenyl]-3-hydroxy-propenyl}-5-oxo-pyrrolidin-1-yl)-heptanoic acid;

7-((R)-2-{(E)-3-[3-(3-chloro-phenoxy)-phenyl]-3-hydroxy-propenyl}-5-oxo-pyrrolidin-1-yl)-heptanoic acid;

4-{2-[(R)-2-((E)-3-Hydroxy-oct-1-enyl)-5-oxo-pyrrolidin-1-yl]-ethyl}-benzoic acid;

4-{2-[(R)-2-((E)-3-Hydroxy-oct-1-enyl)-5-oxo-pyrrolidin-1-yl]-ethyl}-benzoic acid ethyl ester;

4-{3-[(R)-2-((E)-3-Hydroxy-oct-1-enyl)-5-oxo-pyrrolidin-1-yl]-propyl}-benzoic acid;

3-{3-[(R)-2-((E)-3-Hydroxy-oct-1-enyl)-5-oxo-pyrrolidin-1-yl]-propyl}-benzoic acid;

2-{3-[(R)-2-((E)-3-Hydroxy-oct-1-enyl)-5-oxo-pyrrolidin-1-yl]-propyl}-benzoic acid;

1-{2-[(R)-2-((E)-3-Hydroxy-oct-1-enyl)-5-oxo-pyrrolidin-1-yl]-ethyl}-1H-pyrazole-4-carboxylic acid;

4-(2-{(S)-2-[(R)-3-(4'-Chloro-2'-methyl-biphenyl-3-yl)-3-hydroxy-propyl]-5-oxo-pyrrolidin-1-yl}-ethyl)-benzoic acid; and 5-[(R)-2-((E)-3-Hydroxy-oct-1-enyl)-5-oxo-pyrrolidin-1-yl]-ethyl)-thiophene-2-carboxylic acid.

* * * * *